US011712171B2

(12) United States Patent
Malinin et al.

(10) Patent No.: US 11,712,171 B2
(45) Date of Patent: Aug. 1, 2023

(54) ELECTROMAGNETIC DYNAMIC REGISTRATION FOR DEVICE NAVIGATION

(71) Applicant: St. Jude Medical, Cardiology Division, Inc., St. Paul, MN (US)

(72) Inventors: Yuriy Malinin, Edina, MN (US); Anthony D. Hill, Minneapolis, MN (US); Cable P. Thompson, St. Paul, MN (US); Linda Ruetz, New Brighton, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 758 days.

(21) Appl. No.: 15/187,286

(22) Filed: Jun. 20, 2016

(65) Prior Publication Data
US 2016/0367168 A1 Dec. 22, 2016

Related U.S. Application Data

(60) Provisional application No. 62/182,200, filed on Jun. 19, 2015.

(51) Int. Cl.
*A61B 5/06* (2006.01)
*A61B 18/14* (2006.01)
(Continued)

(52) U.S. Cl.
CPC .............. *A61B 5/066* (2013.01); *A61B 5/062* (2013.01); *A61B 5/068* (2013.01);
(Continued)

(58) Field of Classification Search
CPC ......... A61B 5/066; A61B 5/068; A61B 5/062; A61B 34/20; A61B 90/37; A61B 18/1492;
(Continued)

(56) References Cited

U.S. PATENT DOCUMENTS 6,104,944 A * 8/2000 Martinelli ................ A61B 5/06
128/899
6,233,476 B1 5/2001 Strommer et al.
(Continued)

FOREIGN PATENT DOCUMENTS

CN 1903122 A 1/2007
CN 101449292 A 6/2009
(Continued)

OTHER PUBLICATIONS

"Communication Pursuant to Article 94(3) EPC dated Sep. 20, 2022", 8 Pages.
(Continued)

*Primary Examiner* — Jonathan Cwern
(74) *Attorney, Agent, or Firm* — Billion & Armitage

(57) ABSTRACT

A location of a number of fiducial points can be computed. The fiducial points can include impedance locations of an electrode disposed on a catheter in an impedance based coordinate system and magnetic locations of a magnetic position sensor disposed on the catheter in a magnetic based coordinate system. The impedance location of the electrode in the impedance based coordinate system can be transformed into a transformed impedance location of the electrode in the magnetic based coordinate system. A magnetic location of the electrode in the magnetic based coordinate system can be determined. A determination of whether an impedance shift exists between the transformed impedance location of the electrode in the magnetic based system and the magnetic location of the electrode in the magnetic based system can be made. An electromagnetic dynamic registration can be generated between the impedance based coordinate system and the magnetic based coordinate system based on the impedance shift.

14 Claims, 8 Drawing Sheets

(51) Int. Cl.
*A61B 34/20* (2016.01)
*A61B 90/00* (2016.01)
*A61B 17/00* (2006.01)

(52) U.S. Cl.
CPC .......... *A61B 18/1492* (2013.01); *A61B 34/20* (2016.02); *A61B 90/37* (2016.02); *A61B 2017/00292* (2013.01); *A61B 2017/00699* (2013.01); *A61B 2017/00703* (2013.01); *A61B 2017/00725* (2013.01); *A61B 2017/00734* (2013.01); *A61B 2034/2051* (2016.02); *A61B 2034/2053* (2016.02); *A61B 2034/2065* (2016.02); *A61B 2034/2072* (2016.02); *A61B 2034/2074* (2016.02)

(58) Field of Classification Search
CPC .. A61B 2034/2065; A61B 2017/00703; A61B 2034/2051; A61B 2017/00699; A61B 2017/00292; A61B 2034/2074; A61B 2034/2053; A61B 2017/00734; A61B 2017/00725; A61B 2034/2072
See application file for complete search history.

(56) References Cited

U.S. PATENT DOCUMENTS

| | | |
|---|---|---|
| 7,197,354 B2 | 3/2007 | Sobe |
| 7,263,397 B2 | 8/2007 | Hauck et al. |
| 7,386,339 B2 | 6/2008 | Strommer et al. |
| 7,536,218 B2 | 5/2009 | Govari et al. |
| 8,744,599 B2 | 6/2014 | Tegg |
| 2007/0060833 A1 | 3/2007 | Hauck |
| 2007/0073179 A1 | 3/2007 | Afonso et al. |
| 2007/0268287 A1* | 11/2007 | Magnin ................. G06T 19/003 345/419 |
| 2008/0161681 A1 | 7/2008 | Hauck |
| 2009/0205403 A1 | 8/2009 | Boese et al. |
| 2011/0105897 A1 | 5/2011 | Kornblau et al. |
| 2011/0158488 A1 | 7/2011 | Cohen |
| 2011/0176746 A1 | 7/2011 | Bucki et al. |
| 2011/0313414 A1* | 12/2011 | Liu ........................ A61B 5/062 606/41 |
| 2012/0004533 A1 | 1/2012 | Peng et al. |
| 2012/0172702 A1 | 7/2012 | Koyrakh et al. |
| 2012/0265054 A1 | 10/2012 | Olson |
| 2012/0302869 A1 | 11/2012 | Koyrakh et al. |
| 2013/0066193 A1 | 3/2013 | Olson et al. |
| 2013/0211206 A1 | 8/2013 | Sands et al. |
| 2013/0267835 A1 | 10/2013 | Edwards |
| 2014/0221803 A1 | 8/2014 | Bar-Tal et al. |
| 2014/0275957 A1 | 9/2014 | Lupotti |
| 2016/0367168 A1 | 12/2016 | Malinin et al. |

FOREIGN PATENT DOCUMENTS

| | | | |
|---|---|---|---|
| CN | 103025242 | A | 4/2013 |
| CN | 103687533 | A | 3/2014 |
| CN | 103813748 | A | 5/2014 |
| CN | 104290730 | A | 1/2015 |
| EP | 2168478 | A1 | 3/2010 |
| EP | 2233070 | B1 | 2/2012 |
| JP | 2007021218 | A | 9/2012 |
| JP | 2014064922 | A | 4/2014 |
| JP | 2014530030 | A | 11/2014 |
| JP | 2014511737 | A | 1/2015 |
| JP | 2018519046 | A | 7/2018 |
| WO | 2007135609 | A2 | 5/2007 |
| WO | 2012001365 | A1 | 1/2012 |
| WO | 2012141775 | A1 | 10/2012 |
| WO | 2013039564 | A2 | 3/2013 |
| WO | 2014028114 | A1 | 2/2014 |
| WO | 2015085011 | A1 | 7/2016 |
| WO | 2016205807 | A1 | 12/2016 |
| WO | 2016205809 | A1 | 12/2016 |

OTHER PUBLICATIONS

"Notice of Reasons for Rejection dated Sep. 20, 2022", 3 Pages.
"Regularization (mathematics)", Oct. 29, 2018, 11 pages.
Bourmaud, Guillaume , et al., "From Intrinsic Optimization to Iterated Extended Kalman Filtering on Lie Groups", J Math Imaging Vis, Jan. 2, 2016, 284-303.
Karlgaard, Christopher D, "Nonlinear Regression Huber—Kalman Filtering and Fixed-Interval Smoothing", Journal of Guidance, Control, and Dynamics, Jan. 8, 2015, 9 pages.

* cited by examiner

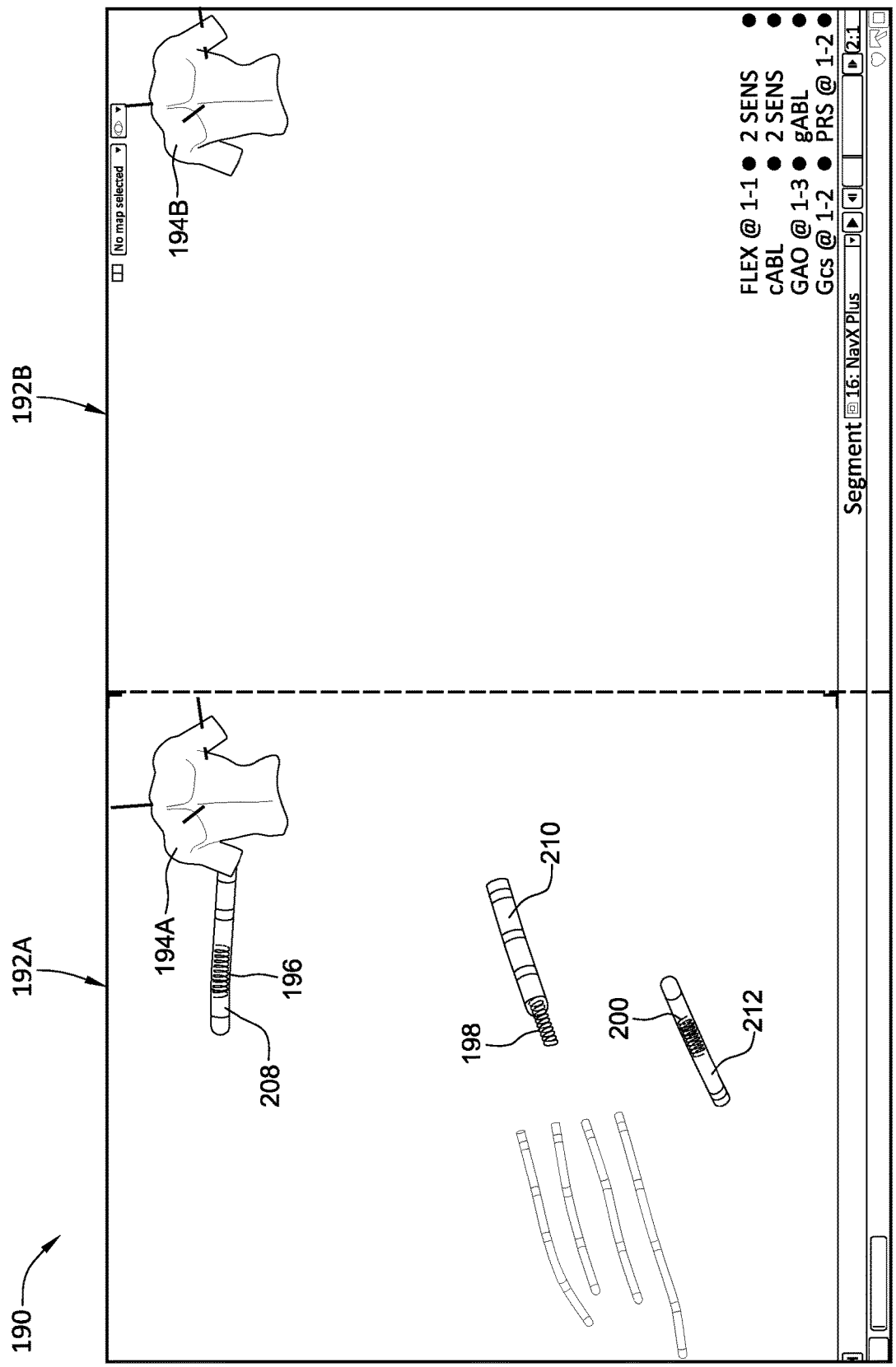

ELECTROMAGNETIC DYNAMIC REGISTRATION FOR DEVICE NAVIGATION

CROSS-REFERENCE TO RELATED APPLICATION

This application is related to PCT/US2016/038387 entitled "ELECTROMAGNETIC DEVICE REGISTRATION FOR DEVICE NAVIGATION", filed 20 Jun. 2015. This application claims priority to U.S. provisional patent application No. 62/182,200 entitled "ELECTROMAGNETIC DEVICE REGISTRATION FOR DEVICE NAVIGATION", filed 19 Jun. 2015, which is hereby incorporated by reference as though fully set forth herein.

BACKGROUND a. Field

The present disclosure relates generally to electromagnetic dynamic registration for device navigation.

b. Background

The three-dimensional coordinates of a catheter or other medical device moving within a patient's body are often tracked using a localization system (sometimes also referred to as a "mapping system," "navigation system," or "positional feedback system"). These devices typically use magnetic, electrical, ultrasound, and other radiation sources to determine the coordinates of these devices. For example, impedance-based localization systems determine the coordinates of the medical device by interpreting a voltage measured by the medical device as a location within an electrical field.

Each different type of localization system offers certain advantages and disadvantages. For example, an impedance-based localization system offers the ability to track numerous localization elements simultaneously, but is susceptible to inhomogeneities in the electrical field and shift and/or drift resulting from varying impedance regions and other external factors. Likewise, a magnetic-based system offers the advantages of improved homogeneity and less drift than an impedance-based system. Such systems, however, require special sensors to be used as localization elements and, as such, are relatively limited in the number of localization elements that can be simultaneously tracked.

SUMMARY

Various embodiments herein provide a method for registration between impedance and magnetic based coordinate systems. The method can include computing a location of a number of fiducial points. The number of fiducial points can include impedance locations of an electrode disposed on a catheter in an impedance based coordinate system and magnetic locations of a magnetic position sensor disposed on the catheter in a magnetic based coordinate system. The method can include transforming the impedance location of the electrode in the impedance based coordinate system into a transformed impedance location of the electrode in the magnetic based coordinate system. The method can include determining a magnetic location of the electrode in the magnetic based coordinate system. The method can include determining whether an impedance shift and/or drift exists between the transformed impedance location of the electrode in the magnetic based system and the magnetic location of the electrode in the magnetic based system. The method can include generating an electromagnetic dynamic registration between the impedance based coordinate system and the magnetic based coordinate system based on the impedance shift and/or drift.

Various embodiments herein provide a non-transitory computer-readable medium storing instructions to generate a registration between impedance and magnetic based coordinate systems, executable by a processing resource to compute a location of a number of fiducial points. The number of fiducial points can include impedance locations of an electrode disposed on a catheter in an impedance based coordinate system and magnetic locations of a magnetic position sensor disposed on the catheter in a magnetic based coordinate system. A global electromagnetic transformation can be computed based on the location of the number of fiducial points to transform the impedance location of the electrode in the impedance based coordinate system into a transformed impedance location of the electrode in the magnetic based coordinate system. A magnetic location of the electrode in the magnetic based coordinate system can be determined. A determination of whether an impedance shift and/or drift exists between the transformed impedance location of the electrode in the magnetic based system and the magnetic location of the electrode in the magnetic based system can be made. An electromagnetic dynamic registration can be generated between the impedance based coordinate system and the magnetic based coordinate system based on the impedance shift and/or drift. A shift and/or drift corrected location of an electrode on an impedance based medical device can be determined using the electromagnetic dynamic registration.

Various embodiments herein provide a system for generating a registration between impedance and magnetic based coordinate systems. The system can include a first catheter that includes a first electrode and a magnetic position sensor. The system can include a second catheter that includes a second electrode. The system can include a processor and memory storing non-transitory computer-readable instruction, executable by the processor to compute a location of a number of fiducial points. The fiducial points can include impedance locations of the first electrode in an impedance based coordinate system and magnetic locations of the magnetic position sensor in a magnetic based coordinate system. A global electromagnetic transformation can be computed based on the location of the number of fiducial points to transform the impedance location of the first electrode in the impedance based coordinate system into a transformed impedance location of the first electrode in the magnetic based coordinate system. A magnetic location of the first electrode in the magnetic based coordinate system can be determined. A determination of whether an impedance shift and/or drift exists between the transformed impedance location of the first electrode in the magnetic based system and the magnetic location of the first electrode in the magnetic based system can be made. An electromagnetic dynamic registration can be generated between the impedance based coordinate system and the magnetic based coordinate system based on the impedance shift and/or drift. A shift and/or drift corrected location of the second electrode can be determined based on the electromagnetic dynamic registration.

BRIEF DESCRIPTION OF THE DRAWINGS

FIG. 6B depicts a graphical user interface displaying a second step associated with transformation from an impedance based coordinate system to a magnetic based coordinate system, in accordance with embodiments of the present disclosure.

DETAILED DESCRIPTION

Figure 1:
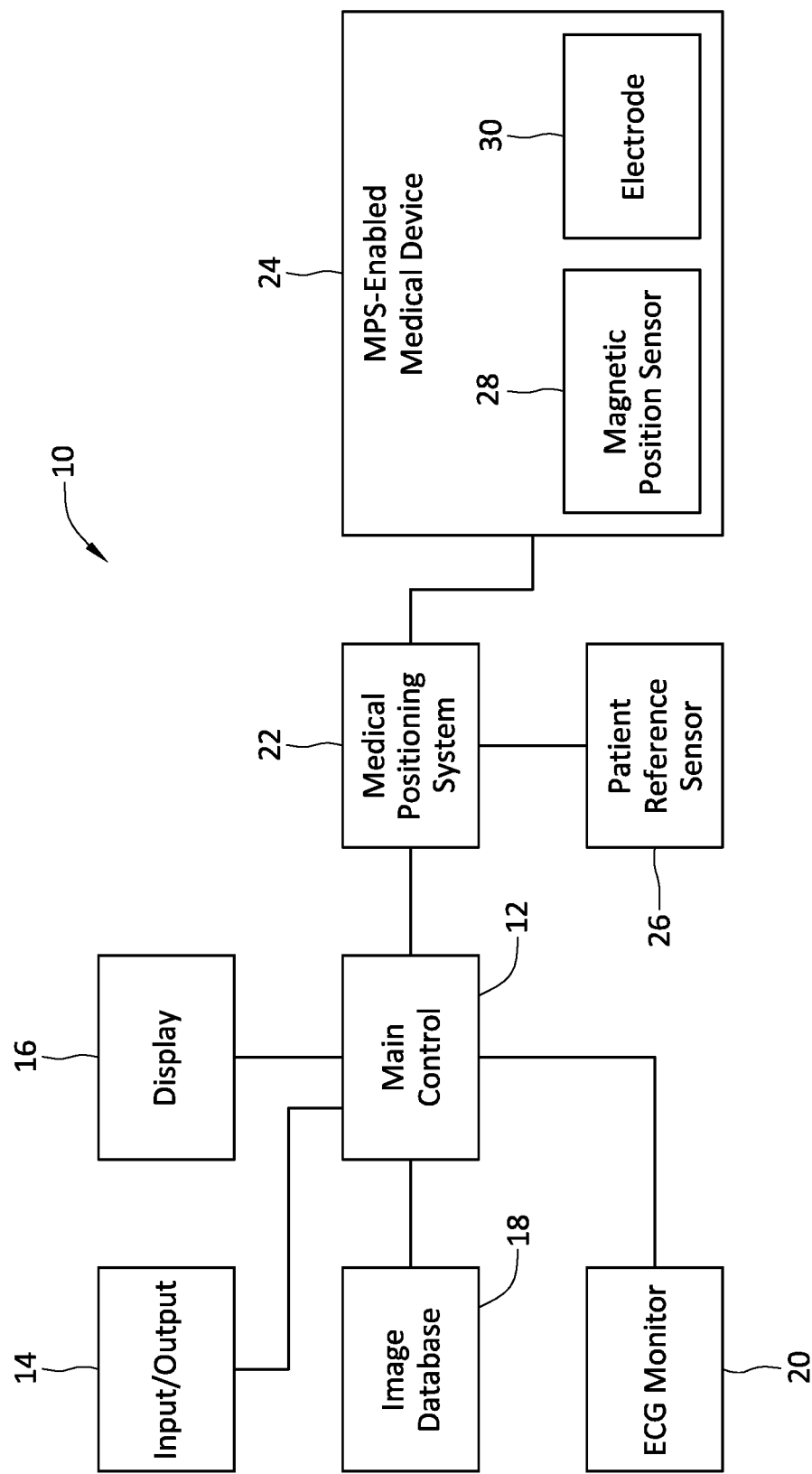
FIG. 1 depicts a schematic and block diagram view of an electromagnetic navigation system, in accordance with embodiments of the present disclosure.

Referring now to the drawings wherein like reference numerals are used to identify identical or similar components in the various views, FIG. 1 is a diagrammatic view of a system 10 in which a medical device, such as a guidewire, catheter, introducer (e.g., sheath) incorporating a magnetic position sensor 28 and an electrode 30 may be used.

Before proceeding to a detailed description of the embodiments of the present disclosure, a description of an exemplary environment in which such devices and sensors may be used will first be set forth. With continued reference to FIG. 1, system 10, as depicted, includes a main electronic control unit 12 (e.g., a processor) having various input/output mechanisms 14, a display 16, an optional image database 18, an electrocardiogram (ECG) monitor 20, a localization system, such as a medical positioning system 22, a medical positioning system-enabled elongate medical device 24, a patient reference sensor 26, a magnetic position sensor 28 and an electrode 30. For simplicity, one magnetic position sensor 28 and one electrode 30 are shown, however, more than one magnetic position sensor 28 and/or more than one electrode 30 can be included in the system 10.

Input/output mechanisms 14 may comprise conventional apparatus for interfacing with a computer-based control unit including, for example, one or more of a keyboard, a mouse, a tablet, a foot pedal, a switch and/or the like. Display 16 may also comprise conventional apparatus, such as a computer monitor.

Various embodiments described herein may find use in navigation applications that use real-time and/or pre-acquired images of a region of interest. Therefore system 10 may optionally include image database 18 to store image information relating to the patient's body. Image information may include, for example, a region of interest surrounding a destination site for medical device 24 and/or multiple regions of interest along a navigation path contemplated to be traversed by medical device 24. The data in image database 18 may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus), wherein the image database acts as a buffer (live fluoroscopy); and/or (3) a sequence of related two-dimensional images defining a cine-loop wherein each image in the sequence has at least an ECG timing parameter associated therewith, adequate to allow playback of the sequence in accordance with acquired real-time ECG signals obtained from ECG monitor 20. It should be understood that the foregoing embodiments are examples only and not limiting in nature. For example, the image database may also include three-dimensional image data as well. It should be further understood that the images may be acquired through any imaging modality, now known or hereafter developed, for example X-ray, ultra-sound, computerized tomography, nuclear magnetic resonance or the like.

ECG monitor 20 is configured to continuously detect an electrical timing signal of the heart organ through the use of a plurality of ECG electrodes (not shown), which may be externally-affixed to the outside of a patient's body. The timing signal generally corresponds to a particular phase of the cardiac cycle, among other things. Generally, the ECG signal(s) may be used by the control unit 12 for ECG synchronized play-back of a previously captured sequence of images (cine loop) stored in database 18. ECG monitor 20 and ECG-electrodes may both comprise conventional components.

Medical positioning system 22 is configured to serve as the localization system and therefore to determine position (localization) data with respect to one or more magnetic position sensors 28 and/or electrodes 30 and output a respective location reading. The location readings may each include at least one or both of a position and an orientation (P&O) relative to a reference coordinate system (e.g., magnetic based coordinate system, impedance based coordinate system), which may be the coordinate system of MPS 22. For some types of sensors, the P&O may be expressed with five degrees-of-freedom (five DOF) as a three-dimensional (3D) position (e.g., a coordinate in three perpendicular axes X, Y and Z) and two-dimensional (2D) orientation (e.g., a pitch and yaw) of an electromagnetic position sensor 28 in a magnetic field relative to a magnetic field generator(s) or transmitter(s) and/or electrode 30 in an applied electrical field relative to an electrical field generator (e.g., a set of electrode patches). For other sensor types, the P&O may be expressed with six degrees-of-freedom (six DOF) as a 3D position (e.g., X, Y, Z coordinates) and 3D orientation (e.g., roll, pitch, and yaw).

Medical positioning system 22 determines respective locations (e.g., P&O) in the reference coordinate system based on capturing and processing signals received from the magnetic position sensor 28 while the sensor is disposed in a controlled low-strength alternating current (AC) magnetic (e.g., magnetic) field and signals received from the electrode 30 while the electrodes are disposed in a controlled electrical field generated by electrode patches, for example.

Each magnetic position sensor 28 and the like may comprise a coil and, from an electromagnetic perspective, the changing or AC magnetic field may induce a current in the coil(s) when the coil(s) are in the magnetic field. The magnetic position sensor 28 is thus configured to detect one or more characteristics (e.g., flux) of the magnetic field(s) in which it is disposed and generate a signal indicative of those characteristics, which is further processed by medical positioning system 22 to obtain a respective P&O for the magnetic sensor 28. The electrode 30 may comprise a ring electrode, in some examples. The electrode 30 can be configured to detect one or more characteristics (e.g., current) of the electrical field(s) in which it is disposed and generate a signal indicative of those characteristics, which is further processed by medical positioning system 22 to obtain a respective P&O for the plurality of electrodes 30.

Referring still to FIG. 1, in an embodiment, medical positioning system 22 may determine the P&O of medical positioning system enabled medical device 24 according to certain physical characteristics of electromagnetic position sensor 28 and electrode 30 in addition to the signals received from magnetic position sensor 28 and electrode 30. Such characteristics may include predetermined calibration data, for example, indicative of or corresponding to the respective winding angles of one or more portions of a coil on sensor 28, the number of coil portions, the type(s) of conductor used in the coil, and the direction and number of loops in the coil. In addition, such characteristics may include predetermined calibration data, for example, indicative of or corresponding to a position of electrode 30, the number of electrodes 30, size of electrode 30, shape of electrode 30, and type of material(s) the electrodes are formed of. Medical positioning system 22 may have such characteristics of the magnetic position sensor 28 and/or electrode 30 pre-programmed, may determine such characteristics from a calibration procedure, or may receive such characteristics from a storage element coupled with medical device 24.

Magnetic position sensor 28 and the electrode 30 may be associated with medical positioning system enabled medical device 24. Another medical positioning system sensor, namely, patient reference sensor (PRS) 26 (if provided in system 10) can be configured to provide a positional reference of the patient's body so as to allow motion compensation for patient body movements, such as respiration-induced movements. Such motion compensation is described in greater detail in U.S. patent application Ser. No. 12/650,932, entitled "Compensation of Motion in a Moving Organ Using an Internal Position Reference Sensor", hereby incorporated by reference in its entirety as though fully set forth herein. PRS 26 may be attached to the patient's manubrium sternum or other location. Like the magnetic position sensor 28, PRS 26 can be configured to detect one or more characteristics of the magnetic field in which it is disposed, wherein medical positioning system 22 determines a location reading (e.g., a P&O reading) indicative of the PRS's position and orientation in the reference coordinate system. In some embodiments, an additional PRS can be configured to detect one or more characteristics of the electrical field in which it is disposed, wherein the medical positioning system 22 determines a location reading (e.g., a P&O reading) indicative of the PRS's position and orientation in the reference coordinate system.

Embodiments of the present disclosure can account for impedance shift and/or drift, associated with the electrode 30. For example, impedance-based navigational systems can be subject to nonlinear shift and/or drift due to numerous physiologic phenomena (e.g., local conductivity changes due to saline or lesions, sweat/patch interactions, changes in lung filling, etc.). Magnetic navigational systems are not subject to these phenomena. By first registering the impedance based coordinate system with the magnetic based coordinate system, impedance shift and/or drift can be detected on a medical device with one or more magnetic position sensors 28 and one or more electrodes 30. Based on the detected shift and/or drift, the accuracy of the magnetic position sensor 28 and magnetic based coordinate system can be conveyed to the impedance based coordinate system. In some embodiments, magnetic position sensors 28 can be expensive to produce and can require more expensive support equipment to operate. Thus, impedance based medical devices that use impedance based sensors (e.g., electrodes 30) for navigation purposes can be preferred over magnetic position sensors 28. In addition, impedance based devices can be more ubiquitous than magnetic based devices, which can lead to a general preference for use of impedance based devices. Embodiments of the present disclosure can provide for navigation of an impedance based device with an accuracy comparable to that associated with a magnetic based device.

In addition, embodiments of the present disclosure can provide advantages over prior methods that use time to detect impedance shift and/or drift. For example, some prior methods are time dependent and detect impedance shift and/or drift based on large changes in impedance locations of electrodes over time (e.g., sudden changes in impedance locations of the electrodes). As such, it can be difficult to distinguish impedance shift and/or drift from manipulation of the electrode and/or catheter equipped with the electrode. For example, the catheter can be moved abruptly over a period of time. Prior methods can classify the abrupt movement as shift, since they rely on time. In addition, time dependent methods may not be able to detect a slow shift and/or drift associated with the impedance location of the electrode. Embodiments of the present disclosure can provide for shift and/or drift detection and/or correction that are time independent.

Figure 2:
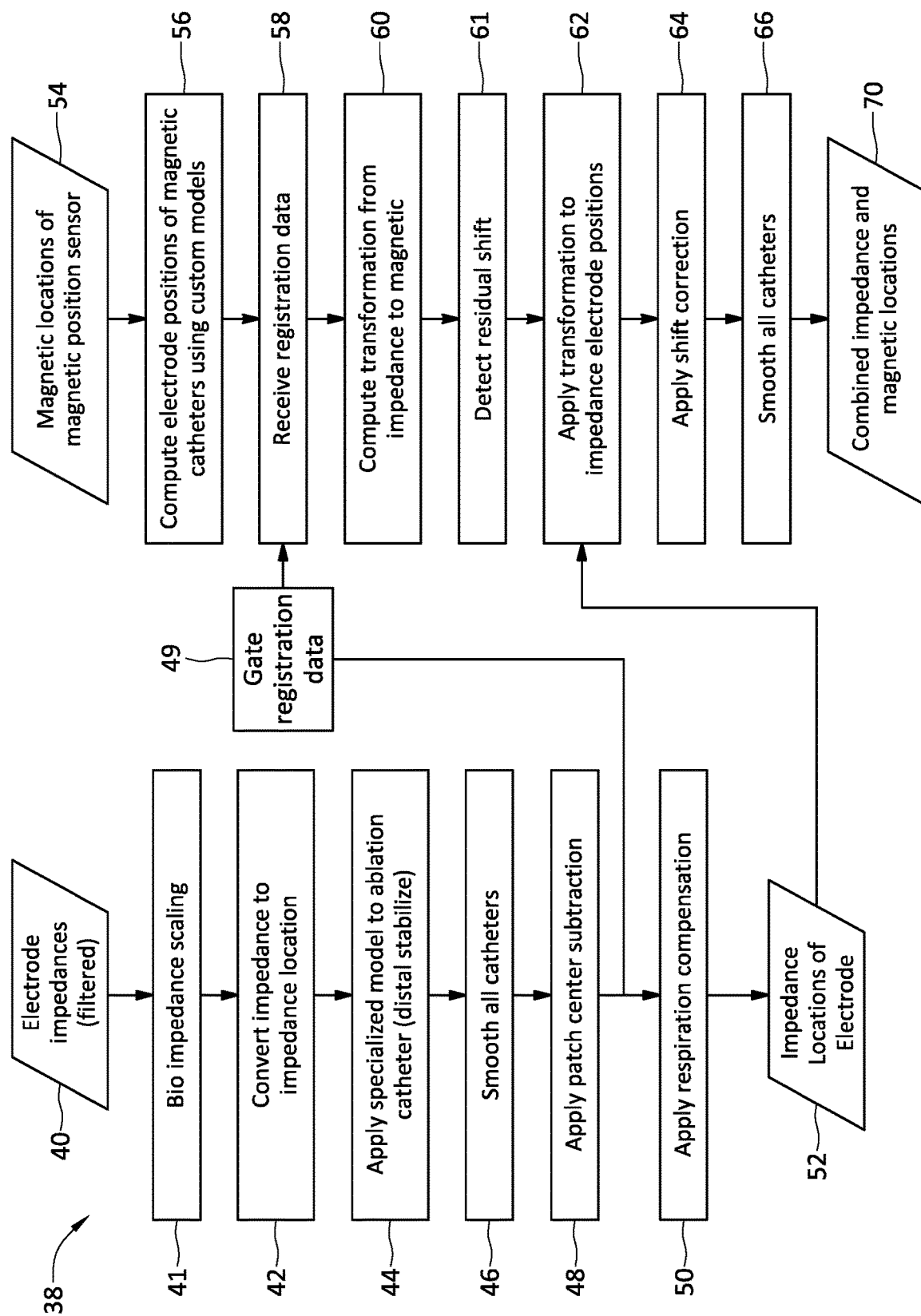
FIG. 2 depicts a flow diagram associated with registering an impedance based coordinate system and a magnetic based coordinate system, in accordance with embodiments of the present disclosure.

FIG. 2 depicts a flow diagram 38 associated with registering an impedance based coordinate system and a magnetic based coordinate system, in accordance with embodiments of the present disclosure. In some embodiments, the flow diagram 38 can include computing a number of fiducial points. The fiducial points can include impedance locations of an electrode 30 and magnetic locations of magnetic position sensor 28. The fiducial points can be collected with a registration catheter, in some embodiments, that includes one or more electrodes 30 and one or more magnetic position sensors 28. At box 40, impedance locations of the electrode 30 can be computed based on an electrode impedance received from the electrode 30. As discussed herein, the medical positioning system 22 can generate an electrical field, which the electrode 30 can be placed in. The electrode 30 can generate an impedance signal based on the strength of the electrical field and the position of the electrode 30 in the electrical field. The impedance signal can be filtered in some embodiments to remove noise from the impedance signal, at box 40. However, in some embodiments, the impedance signal can be unfiltered. Bio impedance scaling can be performed at box 41 to help account for drift in impedance locations (e.g., position values) of the electrode 30, in some embodiments.

The impedance signal can be converted to a location of the electrode 30, at box 42. For example, the impedance signal can be converted to a location of the electrode 30 in an impedance based coordinate system. Field scaling can be performed when converting the impedance signal to the location in the impedance based coordinate system, which can involve multiplying the impedance signals by a factor to obtain the locations in the impedance based coordinate system. For example, a measured inter-electrode spacing at collected geometry points can be used to compensate for inhomogeneities in the electrical field.

In some embodiments, a model can be applied to the catheter (e.g., distal stabilize), at box 44, to ensure that data associated with the impedance locations of the electrode 30 on the catheter correspond to the catheter being in more or less of a straight line or arc. In some embodiments, at box 46, a smoothing function can be applied to the location data received from the one or more electrodes 30 disposed on the catheter. For example, thin plate splines can be applied to the location data to smooth the location data associated with the impedance locations of the electrodes 30. Patch center subtraction can be applied, at box 48, to help reduce shift and/or drift associated with the impedance locations of the electrodes 30. Respiration compensation can be applied at box 50 via data obtained from patient reference sensor 26, as discussed herein, to obtain the impedance locations of the electrodes 30, at box 52.

As discussed, the fiducial points can also include magnetic locations of magnetic position sensor 28. The magnetic locations of the magnetic position sensor 28 can be computed at box 54, based on signals received from the magnetic position sensor 28. A signal can be generated by the magnetic position sensor 28 based on the strength of the magnetic field and the position of the magnetic position sensor 28 in the magnetic field. In some embodiments, a magnetic location of the electrode 30 in the magnetic based coordinate system can be computed at box 56, in some embodiments. In an example, the magnetic location of the electrode 30 in the magnetic based coordinate system can be different than the impedance location of the electrode 30, if shift and/or drift is present. The magnetic location of the electrode 30 can be a determined location of the electrode that is based off of a known location of the one or more magnetic position sensors 28 in the magnetic based coordinate system, in some embodiments. Because the magnetic based coordinate system and the magnetic position sensor 28 are not susceptible to shift and/or drift, the magnetic location of the electrode 30 can reflect a more precise, if not an actual physical location of the electrode 30.

Figure 3A:
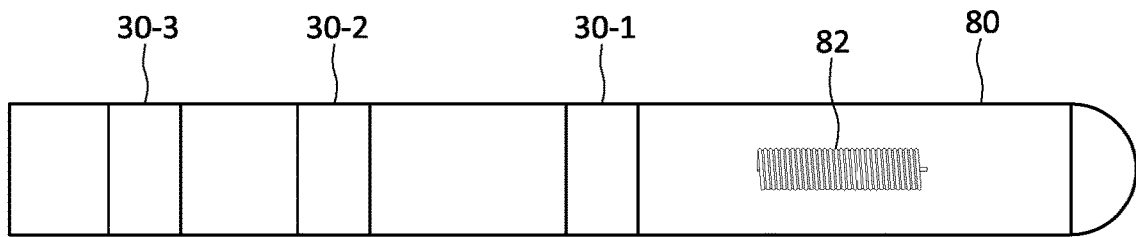
FIG. 3A depicts a side view of a catheter with a magnetic position sensor and electrodes, in accordance with embodiments of the present disclosure.

FIG. 3A depicts a side view of a catheter 80 with a magnetic position sensor 82 and electrodes 30-1, 30-2, 30-3, in accordance with embodiments of the present disclosure. Hereinafter, the electrodes 30-1, 30-2, 30-3 are collectively referred to as electrodes 30-1, 30-2, 30-3. In some embodiments, determining the magnetic location of the electrodes 30-1, 30-2, 30-3 in the magnetic based coordinate system can include transforming the impedance location of the electrodes 30-1, 30-2, 30-3 to the magnetic location of the electrodes 30-1, 30-2, 30-3 using a known distance between the electrodes 30-1, 30-2, 30-3 on the catheter 80 and the magnetic position sensor 82 disposed on the catheter 80 and an orientation of the magnetic position sensor 82 disposed on the catheter. The impedance locations of the electrodes 30-1, 30-2, 30-3 can be used along with a known distance between the electrodes 30-1, 30-2, 30-3 and the magnetic position sensor 82 and the orientation of the magnetic position sensor 82 to determine an impedance location of the magnetic position sensor 82 in the impedance based coordinate system.

Based on the impedance locations of the electrodes 30-1, 30-2, 30-3, a vector can be determined (e.g., best fit to the impedance locations of the electrodes 30-1, 30-2, 30-3) and the impedance location of the magnetic position sensor 82 can be disposed along that vector. In an example, the impedance location of the magnetic position sensor 82 can be spaced apart from the impedance locations of the electrodes 30-1, 30-2, 30-3 along the vector by a known distance between one of the electrodes 30-1, 30-2, or 30-3 and the magnetic position sensor 82. For example, using specifications associated with the catheter (e.g., manufacturer specifications detailing the position of the electrodes 30-1, 30-2, 30-3 with respect to the magnetic position sensor 82), the impedance location of the magnetic position sensor 28 in the impedance based coordinate system can be determined.

In some embodiments, the flow diagram 38 can include transforming the impedance location of the electrodes 30-1, 30-2, 30-3 to the magnetic location of the electrodes 30-1, 30-2, 30-3 using Rodrigues' rotation model. For example, Rodrigues' rotation model can be used to rotate the vector based on the impedance locations of the electrodes 30-1, 30-2, 30-3 in space about the impedance location of the magnetic position sensor 82. For example, the impedance location of the magnetic position sensor 82 can be rotated in space such that an impedance position and orientation of the magnetic position sensor 82 in the impedance based coordinate system aligns with a magnetic position and orientation of the magnetic position sensor 82 in the magnetic coordinate system. As such, the impedance locations (e.g., position and orientation) of the electrodes 30-1, 30-2, 30-3 can be shifted and/or rotated in space and transformed into magnetic locations of the electrodes 30-1, 30-2, 30-3 based on the alignment of the impedance location of the magnetic position sensor 82 (e.g., based off of the known distance between the electrodes 30 and the magnetic position sensor 82) with the magnetic location of the magnetic position sensor 82.

However, use of Rodrigues' rotation model may not incorporate scaling differences between the impedance based coordinate system and the magnetic based coordinate system. For instance, scaling in the impedance based coordinate system can be skewed due to shift and/or drift. For example, a 1 millimeter physical dimension may be skewed such that it is smaller or larger than 1 millimeter in the impedance based coordinate system due to shift and/or drift. Alternatively, dimensions remain consistent and are not skewed in the magnetic based coordinate system. Thus, transformation of the impedance locations of the electrodes 30-1, 30-2, 30-3 in the impedance based coordinate system into the magnetic locations of the electrodes 30-1, 30-2, 30-3 in the magnetic based coordinate system may cause problems with scaling. For instance, using a transformation such as Rodrigues' transformation model, as discussed herein, may result in a spacing between the magnetic locations of the electrodes 30-1, 30-2, 30-3 in the magnetic coordinate system, which is larger or smaller than actual physical dimensions. Thus, the flow diagram can include transforming the impedance location of the electrodes 30-1, 30-2, 30-3 to the magnetic location of the electrodes 30-1, 30-2, 30-3 using a known distance between the electrodes 30-1, 30-2, 30-3 disposed on the catheter and/or a known distance between the electrodes 30-1, 30-2, 30-3 and the magnetic position sensor 28 on the catheter. In an example, the known distance can be associated with a manufacturer's specifications, in some embodiments. Thus, the magnetic locations of the electrodes 30-1, 30-2, 30-3 can be scaled to correct for a change in a distance between the electrodes 30-1, 30-2, 30-3 due to shift and/or drift in the impedance locations of the electrodes 30-1, 30-2, 30-3 in the impedance based coordinate system.

In some embodiments, the flow diagram can include determining the magnetic location of the electrodes in the magnetic based coordinate system based on two five degree-of-freedom magnetic positioning sensors disposed on the catheter. In some embodiments, a catheter can have multiple magnetic sensors (e.g., 2 magnetic sensors) disposed in close relation to one another that are not coaxial with one another to detect a roll of the catheter and/or can have a single magnetic sensor that can detect six degrees-of-freedom to detect a roll of the catheter. In some embodiments, the information associated with the roll of the catheter can be used to determine the magnetic location of the electrodes in the magnetic based coordinate system. In an example, to utilize the roll to create a 6 degree of freedom electromagnetic dynamic registration, a non-collinear arrangement of electrodes can be used on a catheter. For example, either a circular catheter, such as the Reflexion™ catheter produced by St. Jude Medical, Inc.; Inquiry™ Optima™ catheter produced by St. Jude Medical, Inc.; or a catheter such as that described in U.S. Pat. No. 8,900,150, titled Intracardiac Imaging System Utilizing a Multipurpose Catheter, which is hereby incorporated by reference in its entirety, can be used to provide information with six degrees of freedom.

Figure 3B:
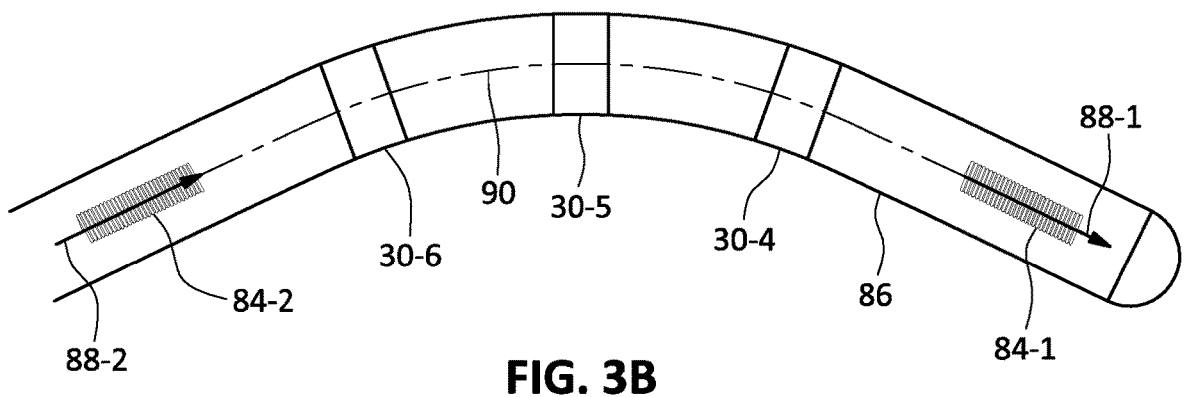
FIGS. 3B and 3C depicts a side view of a catheter with magnetic position sensors in a distal and proximal portion of the catheter with electrodes disposed therebetween, in accordance with embodiments of the present disclosure.

FIG. 3B depicts a side view of a catheter with magnetic position sensors 84-1, 84-2 in a distal and proximal portion of the catheter with electrodes 30-4, 30-5, 30-6 disposed therebetween, in accordance with embodiments of the present disclosure. In some embodiments, determining the magnetic location of the electrodes 30-4, 30-5, 30-6 in the magnetic based coordinate system includes determining a Hermite curve between two five degree-of-freedom magnetic position sensors 84-1, 84-2 disposed in a distal end and a proximal end of the catheter 86 based on a position and orientation of the two five degree-of-freedom magnetic position sensors and a known distance between electrodes 30-4, 30-5, 30-6 disposed on the catheter 86. For instance, based on the position and orientation of each of the magnetic position sensors 84-1, 84-2, a vector 88-1, 88-2 for each of the magnetic position sensors 84-1, 84-2 can be determined in the magnetic coordinate system. In some embodiments, a Hermite curve 90 can be computed between the magnetic position sensors 84-1, 84-2 (e.g., and the vectors 88-1, 88-2). The Hermite curve 90 can be computed based on the startpoint of the curve (e.g., proximal end of vector 88-2) and the direction that the curve leaves the startpoint (e.g., slope of vector 88-2) and the endpoint of the curve (e.g., distal end of vector 88-1) and the direction that the curve meets the endpoint (e.g., slope of vector 88-1).

Figure 3C:
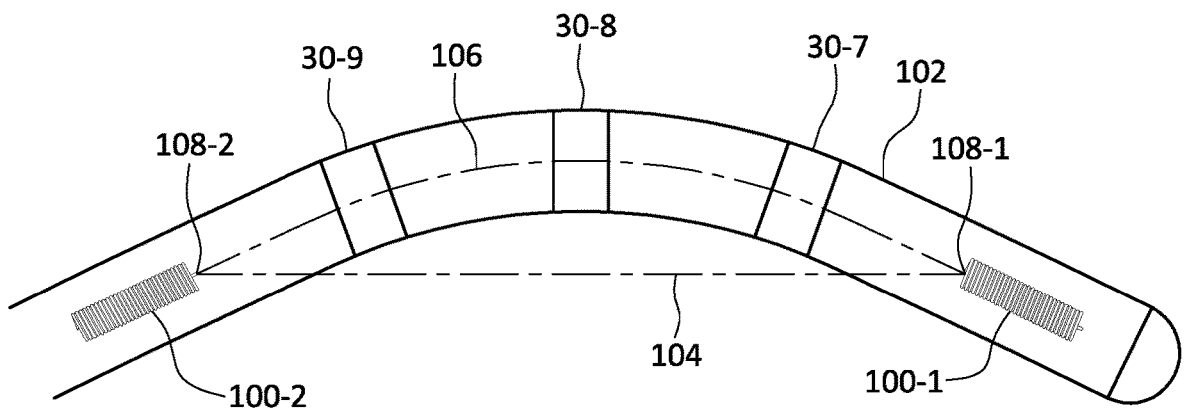

FIG. 3C depicts a side view of a catheter with magnetic position sensors in a distal and proximal portion of the catheter with electrodes disposed therebetween, in accordance with embodiments of the present disclosure. In some embodiments, the flow diagram can include determining the magnetic location of the electrodes 30-7, 30-8, 30-9 in the magnetic based coordinate system by computing an arc length between two magnetic position sensors 100-1, 100-2 (e.g., two five degree-of-freedom sensors). In some embodiments, a first magnetic position sensor 100-1 is disposed in a distal end of the catheter 102 and a second magnetic position sensor 100-2 is disposed in a proximal end of the catheter 102. In an example, a known distance between the two magnetic position sensors 100-1, 100-2 can be used to determine the positions of the electrodes 30-7, 30-8, 30-9. In some embodiments, the known distance between the two magnetic position sensors 100-1, 100-2 can be a physical distance that is available from a manufacturer's specifications.

In some embodiments, the magnetic locations of each of the magnetic position sensors 100-1, 100-2 can be determined and based on a linear distance 104 between the magnetic locations of each of the magnetic position sensors 100-1, 100-2, an arc length can be determined which preserves the known physical distance between the two magnetic position sensors 100-1, 100-2. For example, if the catheter is in a straight orientation (i.e., the catheter is not in a deflected state), the distance between the two magnetic position sensors 100-1, 100-2 can be at a maximum length and thus the magnetic locations of the two magnetic position sensors 100-1, 100-2 can be at a maximum length (e.g., a length of the line 104 can be increased over the length depicted in FIG. 3C). In contrast, as the catheter deflects, as depicted in FIG. 3C, a distance between the two magnetic position sensors 100-1, 100-2 can decrease and thus the magnetic locations of the two magnetic position sensors 100-1, 100-2 can approach a minimum length (e.g., a length of the line 104 can be decreased over the length depicted in FIG. 3C).

However, an arc length between the two magnetic position sensors 100-1, 100-2 and the magnetic locations of the two magnetic position sensors 100-1, 100-2 can remain the same regardless of how little or how much the catheter 102 is deflected. As such, an arc length 106 can be fit between end points 108-1, 108-2. In an example, the arc length has a same length as a distance between the magnetic position sensors 100-1, 100-2 when the catheter 102 is in a straight orientation. Each of the end points can be located at the magnetic location of each of the magnetic position sensors 100-1, 100-2. For example, the first end point 108-1 can be located at a most proximal portion of the first magnetic position sensor 100-1 and the second end point 108-2 can be located at a most distal portion of the second magnetic position sensor 100-2, as depicted in FIG. 3C. Alternatively, the end points 108-1, 108-2 can be located in the middle of each magnetic position sensor 100-1, 100-2 (e.g., between proximal and distal ends of each magnetic position sensor). Alternatively, the end points 108-1, 108-2 can be located at the most distal portion of the first magnetic position sensor 100-1 and at the most proximal portion of the second magnetic position sensor 100-2.

In some embodiments, the fitted arc length 106 can be defined by a model (e.g., polynomial function) that is created based on a construction of the catheter. For example, based on the construction of the catheter, the catheter can deflect in a known manner (e.g., with a known radius of curvature) between the magnetic position sensors 100-1, 100-2. In some embodiments, the model can be created based on experimental results. For example, the portion of the catheter 102 between the magnetic position sensors 100-1, 100-2 can be deflected and a polynomial function can be determined, which best fits the radius of curvature of the catheter over various states of deflection.

Based on the fitted arc length 106, the magnetic positions of the electrodes 30-7, 30-8, 30-9 can be determined. For example, manufacturer specifications can specify a distance between the first magnetic position sensor 100-1, each of the electrodes 30-7, 30-8, 30-9, and/or the second position sensor 100-2. The distances between the first magnetic position sensor 100-1, each of the electrodes 30-7, 30-8, 30-9, and/or the second position sensor 100-2 can be preserved along the arc length 106, as the catheter 102 is deflected, even though a linear distance (e.g., linear distance 104) between the first magnetic position sensor 100-1 and the second magnetic position sensor 100-2 is decreased as the catheter 102 is deflected. Accordingly, based on the magnetic locations of the magnetic position sensors 100-1, 100-2, the magnetic locations of the electrodes 30-7, 30-8, 30-9 can be determined via the arc length 106 and a known physical distance between the first magnetic position sensor 100-1, each of the electrodes 30-7, 30-8, 30-9, and/or the second magnetic position sensor 100-2 (e.g., obtained from manufacturer's specifications).

In some embodiments, the magnetic location of electrodes 30-7, 30-8, 30-9 can be determined based on a biarc curve. In some embodiments, the catheter 102 can include the first magnetic position sensor 100-1 disposed at the distal end of the catheter 102 and the second magnetic position sensor 100-2 disposed proximally of the first magnetic position sensor 100-1. In some embodiments, based on a position and orientation of the magnetic position sensors 100-1, 100-2, a biarc curve can be calculated to represent a deflection of the catheter 102 between the two magnetic position sensors 100-1, 100-2. In an example, a biarc curve can be a curve that consists of two contiguous circular arcs with an identical tangent at their junction point. In some embodiments, the arcs can be in different planes and have different radii. In an example, end points 108-1, 108-2 can each be placed on one of the circular arcs and a number of different biarc curves can be constructed to meet the end point constraints. The number of biarc curves can have the same or different arc lengths in some embodiments, depending on the deflection of the catheter 102 between the two magnetic position sensors 100-1, 100-2. A determination of the catheter segment length can be made by appropriate selection of control points for each arc.

In some embodiments, the magnetic location of electrodes 30-4, 30-5, 30-6 can be determined using a known physical distance between the electrodes 30-4, 30-5, 30-6. As discussed herein, the known physical distance between the electrodes can be provided by manufacturer's specifications, in some embodiments. The magnetic locations of the electrodes 30-4, 30-5, 30-6 can be further refined using impedance locations of the electrodes 30-4, 30-5, 30-6 in the impedance based coordinate system and a least squares method to minimize a difference between the impedance locations of the electrodes 30-4, 30-5, 30-6 and the magnetic locations of the electrodes 30-4, 30-5, 30-6.

In some embodiments, determining the magnetic location of an electrode 30 in the magnetic based coordinate system can include determining a magnetic location of the electrode 30 based on an affine transformation between the impedance based coordinate system and the magnetic based coordinate system. In an example, an Extended Kalman filter can be used to infer hidden state variables corresponding to an affine transformation (or some reflection-free subset) between impedance and magnetic coordinate systems. In some embodiments, magnetic positions of electrodes as well as a full sixth degree-of-freedom rigid body transformation of a full affine transformation that locally moves a domain from the magnetic based coordinate system to the impedance based coordinate system can be incorporated, in addition to hidden state variables. From the hidden state variables, at any time, hidden state measurements (e.g., impedance locations of the electrodes and magnetic location of the five degree-of-freedom sensor coil) can be predicted and estimates of the state variables can be updated using an Extended Kalman filter framework in a fashion that allows updates to those parts of the hidden state variables that are accessible. Thus, at any instant in time, while there may not be enough information to determine parts of state variables, by using the Extended Kalman filter framework, predictions associated with appropriate parts of the state variables associated with the transformation from an impedance based domain to a magnetic based domain can be made.

Differences between the predictions for the appropriate parts of the state variables associated with the transformation and actual measurements can be made and the appropriate parts of the state variables can be updated based on the differences between the predictions and the actual measurements. As such, the state variables can be modified over a given period of time, rather than at a given instant in time. For example, the prior prediction of the appropriate parts of the state variables can be corrected based on measurements at a current time point. In some embodiments, the electrodes 30 can provide measurements in the impedance based coordinate system and a single magnetic position sensor 28 can provide measurements in the magnetic coordinate system. In some embodiments, the state variables are local and apply only to the locations of sensors on a single catheter. Thus, multiple catheters can each be described by distinct state variables. In some embodiments, the state variables for each catheter can include catheter shape (e.g., a small number of curvature and torsions along a Frenet-Serret reference frame), a unit quaternion and translation to describe the catheter shape, and/or position and orientation in an undistorted patient reference frame.

Additionally, in some embodiments, the magnetic locations of the electrodes 30 can be determined based on a position and orientation of one or more magnetic position sensors 28. For example, based on a position and orientation of a magnetic position sensor 28, a vector for the magnetic position sensor can be determined. In some embodiments, the vector can be in a direction facing towards the distal end of the magnetic position sensor 28 (e.g., magnetic coil) and can be coaxial with the magnetic position sensor 28. Because the magnetic position sensor 28 is disposed within a shaft of a catheter, the position and orientation of the catheter shaft can be determined based on the vector associated with the magnetic position sensor. In some embodiments, specifications associated with a positioning of one or more electrodes 30 on the shaft with respect to the magnetic position sensor 28 (e.g., manufacturer specifications) can be used to determine the magnetic position of the electrodes 30. For instance, the magnetic positions of the electrodes 30 can be extrapolated using the known magnetic position and orientation of magnetic position sensor 28 and a known spacing of the electrodes 30 with respect to the magnetic position sensor 28. Determination of the magnetic position of the electrodes 30 in this way can provide for an increased dimensional accuracy, no impedance shift and/or drift, and no distortion during radio frequency ablation, in some examples. Determination of the magnetic position of the electrodes 30 in this manner can be beneficial in ventricular tachycardia cases where only an ablation catheter is present, in some embodiments. Determination of the magnetic position of the electrodes 30 in this manner can accommodate a second magnetic position sensor for catheter shaft visualization.

In some embodiments, the flow diagram can include receiving registration data at box 58. In an example, receiving the registration data can include receiving the impedance locations of the electrodes 30 after the patch center subtraction has been applied to the impedance locations of the electrodes 30, but prior to the respiration compensation being applied to the impedance locations of the electrodes 30. In some embodiments, the impedance locations of the electrodes 30 (e.g., registration data) can be gated to a specific interval of a ventilatory phase, at box 49. For example, the impedance locations of the electrodes 30 can be correlated with the specific interval of ventilatory phases. In addition, receiving the registration data can include receiving the magnetic locations of the electrodes 30. For example, as discussed herein, the magnetic locations of the electrodes 30 can be determined in the magnetic based coordinate system. The registration data can be collected so the magnetic locations of the electrodes 30 can be registered with the impedance locations of the electrodes 30 (e.g., displayed in one coordinate system).

In some embodiments, the flow diagram 38 can include computing a transformation of the registration data from the impedance based coordinate system to the magnetic based coordinate system at box 60. In some embodiments, the received impedance locations of the electrodes 30 (e.g., that have had patch center subtraction applied) can be compared to the magnetic positions of the electrodes 30 and the impedance based coordinate system and the magnetic based coordinate system can be aligned. A magnetic location that corresponds to the impedance location of the electrodes 30 in the magnetic coordinate system can then be determined. For example, the impedance based coordinates of the impedance location of the electrodes 30 can be transformed into magnetic based coordinates. In an example, the registration data can include both impedance locations of the electrodes 30 in the impedance based coordinate system and magnetic locations of the electrodes 30 in the magnetic based coordinate system. Based on the transformation, the locations of the electrodes 30 can be registered (e.g., combined) in one coordinate system (e.g., magnetic based coordinate system). In an example, Rodrigues' transformation model, an Extended Kalman filter, and/or other methodology discussed herein can provide an instantaneous registration between the impedance based coordinate system and the magnetic based coordinate system. In some embodiments, the flow diagram can include detecting a residual shift and/or drift associated with the impedance location of the electrodes 30, at box 61. For example, a determination can be made of whether any additional shift and/or drift has occurred and/or whether any shift and/or drift still exists, which is unaccounted for.

In some embodiments, the flow diagram 38 can include applying the transformation to the impedance locations of the electrodes 30, at box 62. In an example, applying the transformation can include transforming the impedance locations of the electrodes 30 in the impedance based coordinate system into transformed impedance locations of the electrodes 30 in the magnetic based coordinate system. In some embodiments, the transformation can be computed using the received impedance locations of the electrodes 30 that have had patch center subtraction applied, while the transformation is applied to the impedance locations of the electrodes 30 that have had respiration compensation applied.

In some embodiments, the electromagnetic dynamic registration can be sensitive to location artifacts. While respiration compensation is meant to reduce location artifacts introduced by breathing, it may not do so perfectly. Sometimes respiration compensation can be incomplete and occasionally it may introduce its own artifacts. Consequently, the electromagnetic dynamic registration corresponding to a specific interval of the ventilatory phase can be computed: between end-expiration and begin-inspiration. This can be done in a gated fashion, which can eliminate any potential artifacts introduced by breathing and may not substantially impact the time to acquire a registration. At the same time, it may not be desirable to gate the update of catheter positions, as visualized by an end user. Thus, respiration compensation could be applied instead of gating in those cases. This can allow for an artifact-free registration and continuous position updates.

In some embodiments, the flow diagram can include determining whether an impedance shift and/or drift exists between the transformed impedance location of the electrode 30 in the magnetic based system and the magnetic location of the electrode in the magnetic based system. As discussed herein, nonlinear shift and/or drift of the impedance location of the electrodes can be due to numerous physiologic phenomena (e.g., local conductivity changes due to saline or lesions, sweat/patch interactions, changes in lung filling, etc.). Because the magnetic position sensors 28 are not subject to shift and/or drift, the computed magnetic locations of the electrodes 30 also may not be subject to shift and/or drift. As such, the difference between the location of the transformed impedance location of the electrode 30 in the magnetic based coordinate system and the magnetic location of the electrode can be equivalent to a shift and/or drift of the impedance location of the electrode 30.

In some embodiments, to determine whether the shift and/or drift of the impedance location of the electrode has occurred, the initial number of fiducial points can be collected. In an example, the initial number of fiducial points can be collected via a registration catheter with the one or more magnetic position sensors 28 and the one or more electrodes 30 disposed thereon. In some embodiments, the catheter can be quickly swiped through a volume of interest to collect an initial number of fiducial points. Based on the initial number of fiducial points, the determination of whether the impedance locations of the electrodes 30 have shifted and/or drifted can be determined. However, in some embodiments, a greater number of fiducial points can be collected to determine whether the impedance locations of the electrodes 30 have shifted and/or drifted.

In some embodiments, when the initial number of fiducial points that are collected includes a small number of fiducial points, a determination of whether shift and/or drift has occurred can be made. If a determination has been made that shift and/or drift has occurred, an indication can be provided to a user to collect an additional number of fiducial points to be used for determination of an amount of the shift and/or drift and application of a shift and/or drift correction. Thus, if shift and/or drift has not occurred, the user may not have to spend additional time collecting additional fiducial points for the determination of the shift and/or drift, which can result in use of fewer resources. In some embodiments, a greater number of fiducial points can initially be collected and the shift and/or drift correction can be determined without collecting additional fiducial points.

When an additional number of fiducial points are collected, an amount of received registration data can increase. As a result, an electromagnetic dynamic registration that is computed from the registration data can change as the additional number of fiducial points are computed and added to the registration data. As such, shift and/or drift corrected locations of the electrodes 30 that are determined from the initially collected fiducial points can change in response to the additional data being processed to determine shift and/or drift associated with the impedance location of the electrodes 30. For example, because the electromagnetic dynamic registration is dynamic and can change (e.g., a different amount of shift and/or drift can exist), the electromagnetic dynamic registration can initially be computed using a small number of fiducial points, collected in a relatively small volume. An additional number of fiducial points that are collected can have a large effect on the parameters of registration. Impedance electrode 30 locations that are located outside of the initially collected fiducial points can undergo large movements as an additional number of fiducial points are collected. As such, dynamically updating the electromagnetic dynamic registration (e.g., determining a secondary dynamic electromagnetic dynamic registration) with the additional number of fiducial points can cause shift and/or drift corrected locations of the electrodes 30 on the impedance based medical device to change as the additional number of fiducial points are added. For example, registering an impedance location of the electrodes 30 on the impedance based medical device with the magnetic based coordinate system based on the secondary electromagnetic dynamic registration can cause the shift and/or drift corrected locations of the electrodes 30 on the impedance based medical device to change.

Accordingly, embodiments of the present disclosure can include transitioning between the electromagnetic dynamic registration and the updated electromagnetic dynamic registration via a smoothing function. In some embodiments, the smoothing function can include thin plate splines. In some embodiments, given fiducial pairs X→Y the thin plate splines can be represented via the following:

$$\begin{bmatrix} K_X^T \\ 1^{n^T} \\ X^T \end{bmatrix} Y = \begin{bmatrix} K_X^T \\ 1^{n^T} \\ X^T \end{bmatrix} [K_X \ 1^n \ X] \begin{bmatrix} W \\ t \\ A \end{bmatrix}$$

In some embodiments, U(r) can be dependent on the dimensionality of the spline. For 2-dimensional, $U(r)=r^2 \log r$, and for 3-dimensional, $U(r)=|r|$. W, t, and A can be solved for in some embodiments. Usage of the solution can be expressed as:

$$R_{ij} = U(|P_i - X_j|)$$

$$TPS(P) = [R \ 1^n \ P] \begin{bmatrix} W \\ t \\ A \end{bmatrix}$$

The spine can go through all control points, represented as:

$$TPS(X)=Y$$

In some embodiments, a stiffness ($\lambda_S$) can be added to the solution, which can be represented as:

$$\begin{bmatrix} K_X^T \\ 1^{n^T} \\ X^T \end{bmatrix} Y = \left( \begin{bmatrix} K_X^T \\ 1^{n^T} \\ X^T \end{bmatrix} [K_X \ 1^n \ X] + \frac{n}{n_c} \lambda_S \begin{bmatrix} K_C & 0^n & 0^{n,m} \\ 0^{n^T} & 0 & 0^{m^T} \\ 0^{m,n} & 0^m & 0^{m,m} \end{bmatrix} \right) \begin{bmatrix} W \\ t \\ A \end{bmatrix}$$

The addition of the stiffness can improve a condition of the matrix. Further, because the stiffness is added to the solution, the stiffness spline is not forced through control points.

In some embodiments, an affine regularization term ($\lambda_A$) can be added to the solution, which can be represented as:

$$\begin{bmatrix} K_X^T \\ 1^{n^T} \\ X^T \end{bmatrix} Y + \begin{bmatrix} 0^{n,m} \\ 0^{m^T} \\ \lambda_2 I \end{bmatrix} = \left( \begin{bmatrix} K_X^T \\ 1^{n^T} \\ X^T \end{bmatrix} [K_X \ 1^n \ X] + \begin{bmatrix} \frac{n}{n_c} \lambda_S K_C & 0^n & 0^{n,m} \\ 0^{n^T} & 0 & 0^{m^T} \\ 0^{m,n} & 0^m & \lambda_A I \end{bmatrix} \right) \begin{bmatrix} W \\ t \\ A \end{bmatrix}$$

Addition of the affine regularization term can control extrapolation by adding a cost for differences between A and identity matrix I.

In some embodiments, the flow chart can include generating an electromagnetic dynamic registration between the impedance based coordinate system and the magnetic based coordinate system based on the impedance shift and/or drift. The electromagnetic dynamic registration between the impedance based coordinate system and the magnetic based coordinate system can account for the transformation of the impedance locations of the electrodes 30 in the impedance based coordinate system into the transformed impedance locations of the electrodes 30 in the magnetic based coordinate system and can also account for the impedance shift and/or drift associated with the impedance locations of the electrodes 30. Accordingly, impedance locations of the electrodes 30 can be received and the electromagnetic dynamic registration can be used to transform the impedance locations of the electrodes 30 into the magnetic based coordinate system and correct for the shift and/or drift, which can be associated with the impedance locations of the electrodes 30. In an example, impedance shift and drift detection and correction can be performed via the electromagnetic dynamic registration, as detailed in the application, Ser. No. 15/187,322 titled "Impedance Shift and Drift Detection and Correction", filed 20 Jun. 2016 and in application, no. PCT/US2016/038402 titled "Impedance Shift and Drift Detection and Correction", filed 20 Jun. 2016, which are both hereby incorporate by reference in their entirety.

In some embodiments, the electromagnetic dynamic registration can be generated for a volume of interest (e.g., chamber of the heart). In an example, as discussed herein, the registration catheter with the magnetic position sensors 28 and the electrodes 30 disposed thereon can be used to gather data for the generation of the electromagnetic dynamic registration. In some embodiments, once the electromagnetic dynamic registration has been generated for the volume of interest, the registration catheter with the magnetic position sensors 28 and the electrodes 30 can be removed from the volume of interest. In some embodiments, an impedance based medical device, which can be a catheter that includes electrodes 30 and no magnetic position sensors 28, can be inserted in the volume of interest. The electromagnetic dynamic registration can then be used to register an impedance location of an electrode 30 on the impedance based medical device with the magnetic based coordinate system using the electromagnetic dynamic registration and a shift and/or drift associated with the impedance location of the electrodes 30 can be accounted for via the electromagnetic dynamic registration.

In some embodiments, the flow chart can include applying the shift and/or drift correction, at box 64, to determine a shift and/or drift corrected location of the electrodes 30 on the impedance based medical device. As discussed herein, in some embodiments, the impedance location of the electrodes 30 can be shifted via the electromagnetic dynamic registration to provide shift and/or drift corrected locations of the electrodes 30 on the impedance based medical device. In some embodiments, a smoothing function can be applied to the shift and/or drift corrected locations of the electrodes 30 on the impedance based medical device, at box 66. The thin plate spline transformation, as discussed herein, may not provide locations of the electrodes 30 that are associated with a representation of a smooth catheter. As such, a smoothing function can be applied to the shift and/or drift corrected locations of the electrodes 30 to provide an improved representation of the catheter. In some embodiments, the shift and/or drift corrected locations of the electrodes 30, the magnetic locations of the electrodes 30, and/or the magnetic locations of the magnetic position sensors 28 can be combined, at box 70. In an example, the flow diagram can include displaying the shift and/or drift corrected locations of the electrodes 30, the magnetic locations of the electrodes 30, and/or the magnetic locations of the magnetic position sensors 28. As such, the location of the impedance based medical device can be displayed based on the registered location of the electrodes 30 with the magnetic based coordinate system. As discussed herein, one or more of the catheters that include the electrodes 30 and/or the magnetic position sensors 28 can be displayed, based on the shift and/or drift corrected locations of the electrodes 30, the magnetic locations of the electrodes 30, and/or the magnetic locations of the magnetic position sensors 28.

Figure 4:
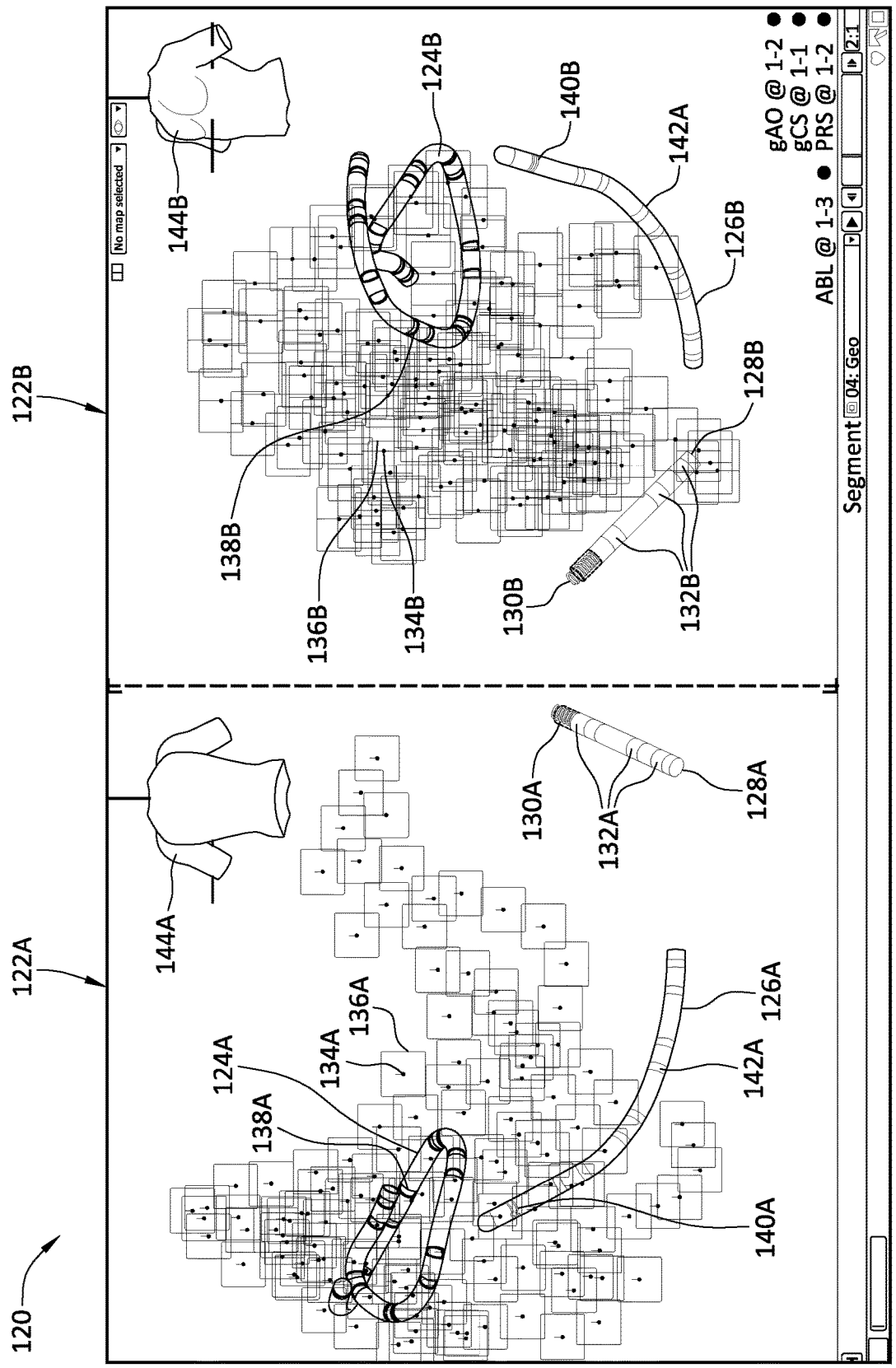
FIG. 4 depicts a graphical user interface displaying a graphical representation of an impedance based catheter, a reference catheter; and a registration catheter, in accordance with embodiments of the present disclosure.

FIG. 4 depicts a graphical user interface 120 displaying a first view 122A of a graphical representation of an impedance based catheter 124A, a reference catheter 126A; and a registration catheter 128A, and a second view 122B of the impedance based catheter 124B, the reference catheter 126B; and the registration catheter 128B, in accordance with embodiments of the present disclosure. The registration catheter 128A, 128B can include a magnetic position sensor 130A, 130B and a number of electrodes 132A, 132B, as discussed herein. The registration catheter 128A, 128B, can be swiped through a volume of interest to collect a number of fiducial points, represented in FIG. 4 as fiducial point 134A, 134B. In some embodiments, as discussed herein, an initial number of fiducial points 134A, 134B can be collected by the registration catheter 128A, 128B.

In some embodiments, the registration catheter 128A, 128B can also be used to collect an additional number of fiducial points, which can be used to update an electromagnetic dynamic registration. In an example, each fiducial point 134A, 134B can be a point in space (e.g., volume of interest) that has been visited by one of the number of electrodes on the registration catheter 128A. A registration boundary 136A, 136B can be defined around each of the fiducial points. The registration boundary 136A, 136B can be a three dimensional space (e.g., defined by a cube) that surrounds each of the fiducial points 134A, 134B. In some embodiments, the registration boundary 136A, 136B can define a spacing within a volume of interest where the fiducial points 134A, 134B are collected. For example, only one fiducial point 134A, 134B can be collected within the registration boundary 136A, 136B. The registration boundary 136A, 136B can provide a minimal distance between fiducial points that are collected. Although some of the registration boundaries 136A, 136B are shown as overlapping in FIG. 4, this is a result of the graphical user interface 120 being displaying as a 3-dimensional representation. The registration boundaries 136A, 136B are depicted as 2-dimensional for simplicity.

In some embodiments, the registration boundaries can prevent too many fiducial points 134A, 134B from being collected in a particular region of the volume of interest. In an example, collection of a greater number of fiducial points 134A, 134B obtained by decreasing a size of the registration boundaries 136A, 136B or not using registration boundaries can result in a tradeoff between an increased accuracy and a longer processing time associated with generation of an electromagnetic dynamic registration. In some embodiments, the size of the registration boundaries 136A, 136B can be increased or decreased to fulfill the needs of or a personal preference of a user. In some embodiments, a selection can be made to turn the registration boundaries off, such that no restrictions are associated with how many fiducial points 134A, 134B are collected in a particular region of the volume of interest.

FIG. 4 depicts an impedance based catheter 124A, 124B that includes a number of electrodes (e.g., one of which is represented as electrode 138A, 138B). In some embodiments, the impedance based catheter 124A, 124B does not include any magnetic position sensors. Thus, an electromagnetic dynamic registration for a volume of interest can be generated and impedance locations of electrodes 138A on the impedance based catheter 124A, 124B can be registered with the magnetic based coordinate system using the electromagnetic dynamic registration and shift and/or drift can be accounted for in the volume of interest. For example, shift and/or drift corrected locations of the electrodes 30 can be determined. Thus, the impedance based catheter 124A, 124B can be more accurately navigated through the volume of interest through use of the electromagnetic dynamic registration.

FIG. 4 further depicts a reference catheter 126A, 126B. The reference catheter can in some embodiments be a Livewire™ catheter, produced by St. Jude Medical, Inc. In some embodiments, the reference catheter 126A, 126B can be used as a reference when performing a procedure (e.g., positional reference), a diagnostic device (e.g., to collect data), and/or a therapeutic device (e.g., ablation therapy device). The reference catheter 126A, 126B can include a magnetic position sensor 140A, 140B, in some embodiments, as well as electrodes (e.g., one of which is represented as electrode 142A, 142B). In some embodiments, as discussed herein, the electromagnetic dynamic registration for the volume of interest can be generated and impedance locations of electrodes 142A on the reference catheter 126A, 126B can be registered with the magnetic based coordinate system using the electromagnetic dynamic registration and shift and/or drift can be accounted for in the volume of interest. Thus, the reference catheter 126A, 126B can be more accurately navigated through the volume of interest through use of the electromagnetic dynamic registration.

As depicted, in FIG. 4, a perspective indicator that is included in the first view 122A and second view 122B can be indicated by perspective indicator 144A and perspective indicator 144B, respectively. For example, the first view 122A is a perspective from a rear angle with respect to a patient's body, which is represented by perspective indicator 144A. The second view 122B is a perspective from a front quartering angle to the patient's body, which is represented by perspective indicator 144B.

Figure 5:
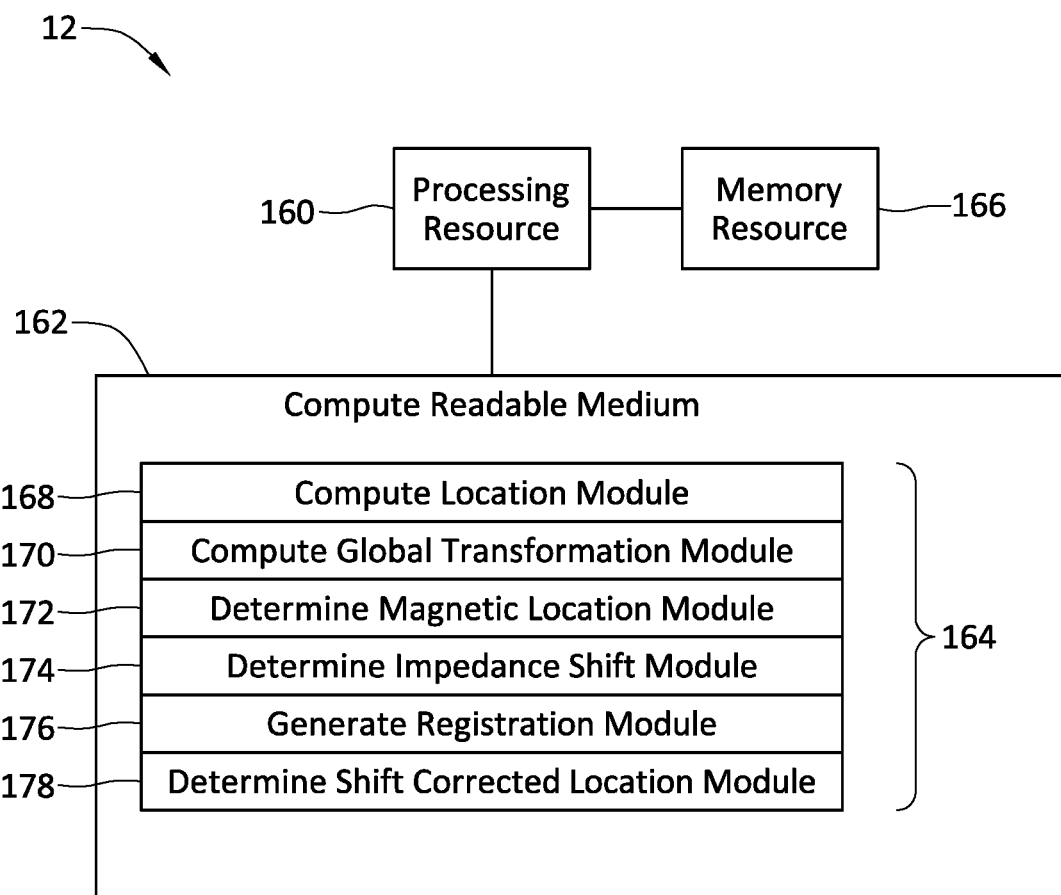
FIG. 5 depicts a block diagram of an example of a computer-readable medium in communication with processing resources of a computing device, in accordance with embodiments of the present disclosure.

FIG. 5 depicts a block diagram of an example of a computer-readable medium in communication with processing resources of a computing device, in accordance with embodiments of the present disclosure. The main control 12, as discussed in relation to FIG. 1, can utilize software, hardware, firmware, and/or logic to perform a number of functions. The main control 12 can include a number of remote computing devices.

The main control 12 can be a combination of hardware and program instructions configured to perform a number of functions. The hardware, for example, can include one or more processing resources 160, computer readable medium (CRM) 162, etc. The program instructions (e.g., computer-readable instructions (CRI) 164) can include instructions stored on CRM 162 and executable by the processing resource 160 to implement a desired function (e.g., determine a shift and/or drift corrected location of an electrode on an impedance based medical device using the electromagnetic dynamic registration, etc.). The CRI 164 can also be stored in remote memory managed by a server and represent an installation package that can be downloaded, installed, and executed. The main control 12 can include memory resources 166, and the processing resources 160 can be coupled to the memory resources 166.

Processing resources 160 can execute CRI 164 that can be stored on an internal or external non-transitory CRM 162. The processing resources 160 can execute CRI 164 to perform various functions, including the functions described with respect to FIG. 1 to FIG. 4.

A number of modules 168, 170, 172, 174, 176, 178 can be sub-modules or other modules. For example, the compute location module 168 and the compute global transformation module 170 can be sub-modules and/or contained within a single module. Furthermore, the number of modules 168, 170, 172, 174, 176, 178 can comprise individual modules separate and distinct from one another.

A compute location module 168 can comprise CRI 164 and can be executed by the processing resource 160 to compute a location of a number of fiducial points. The number of fiducial points can include impedance locations of an electrode 30 disposed on a catheter in an impedance based coordinate system. The fiducial points can also include magnetic locations of a magnetic position sensor 28 disposed on the catheter in a magnetic based coordinate system. In some embodiments, the fiducial points can be collected with a registration catheter that includes a number of electrodes 30 and a number of magnetic position sensors 28. The registration catheter can be swept through a volume of interest that is exposed to an electrical field and a magnetic field, each of which can be produced by the medical positioning system 22. In an example, impedance signals from the electrodes 30 can be received and impedance locations of the electrodes 30 can be computed based on the electrode impedances. In addition, signals can be received from the magnetic position sensors 28 and a magnetic location of the magnetic position sensors 28 can be computed, based on the signals received from the magnetic position sensors 28.

A compute global transformation module 170 can comprise CRI 164 and can be executed by the processing resource 160 to compute a global electromagnetic transformation based on the location of the number of fiducial points to transform the impedance location of the electrodes 30 in the impedance based coordinate system into transformed impedance locations of the electrodes 30 in the magnetic based coordinate system. In an example, the impedance based coordinate system and the magnetic based coordinate system can be aligned and the impedance based coordinates of the impedance locations of the electrodes 30 can be transformed into magnetic based coordinates in the magnetic based coordinate system. The impedance locations of the electrodes 30 can thus be transformed from impedance based coordinates to magnetic based coordinates, such that they can be displayed in magnetic based coordinate system.

A determine magnetic location module 172 can comprise CRI 164 and can be executed by the processing resource 160 to determine magnetic locations of the electrodes 30 in the magnetic based coordinate system. For example, the magnetic locations of the electrodes 30 can be determined in a manner similar to that previously discussed herein.

A determine impedance shift module 174 can comprise CRI 164 and can be executed by the processing resource 160 to determine whether an impedance shift and/or drift exists between the transformed impedance location of the electrode 30 in the magnetic based coordinate system and the magnetic location of the electrode 30 in the magnetic based coordinate system. In some embodiments, the transformed impedance locations of the electrodes 30 can be compared to the magnetic locations of the electrodes 30 to determine whether impedance shift and/or drift has occurred. In an example, impedance shift and/or drift can be determined to have occurred if there is a difference between the transformed impedance locations of the electrodes 30 and the magnetic locations of the electrodes 30. For instance, if the transformed impedance locations of the electrodes 30 have different coordinates than the magnetic locations of the electrodes 30 (e.g., the coordinates are shifted from one another by a defined amount), a determination that an impedance shift and/or drift has occurred can be made.

A generate registration module 174 can comprise CRI 164 and can be executed by the processing resource 160 to generate an electromagnetic dynamic registration between the impedance based coordinate system and the magnetic based coordinate system based on the impedance shift and/or drift. The electromagnetic dynamic registration between the impedance based coordinate system and the magnetic based coordinate system can account for the transformation of the impedance location of the electrodes 30 in the impedance based coordinate system into the transformed impedance location of the electrode in the magnetic based coordinate system and can also account for the impedance shift and/or drift associated with the impedance location of the electrodes 30. Accordingly, impedance locations of the electrodes 30 can be received and the electromagnetic dynamic registration can be used to transform the impedance locations of the electrodes 30 into the magnetic based coordinate system and account for the shift and/or drift, as discussed herein.

As discussed herein, CRI 164 can be provided to determine a secondary electromagnetic dynamic registration in response to a determination that impedance shift and or drift exists. In some embodiments, the secondary electromagnetic dynamic registration can include collecting an additional number of fiducial points (e.g., impedance locations of the electrodes 30 and magnetic locations of the magnetic position sensors 28). The additional number of fiducial points can provide for a more robust electromagnetic dynamic registration. For example, a user can initially swipe a volume of interest with a catheter equipped with magnetic position sensors 28 and electrodes 30 to collect a first set of fiducial points, as discussed herein, for construction of the electromagnetic dynamic registration and for determination of whether shift and/or drift has occurred. If shift and/or drift has occurred, the user can perform a more thorough exploration of the volume of interest to obtain a second set of fiducial points for construction of the secondary electromagnetic dynamic registration.

In some embodiments, CRI 164 can be provided to register an impedance location of the electrode on the impedance based medical device with the magnetic based coordinate system, based on the secondary electromagnetic dynamic registration. For example, the impedance locations of the electrodes 30 can be registered with the secondary electromagnetic dynamic registration to obtain a shift and/or drift corrected locations of the electrodes 30. As such, any impedance shift and/or drift associated with the impedance locations of the electrodes 30 can be corrected, as a result of registering the impedance locations of the electrodes 30 with the secondary electromagnetic dynamic registration to determine shift and/or drift corrected locations of the electrodes.

A determine shift corrected location module 174 can comprise CRI 164 and can be executed by the processing resource 160 to determine shift and/or drift corrected locations of electrodes 30 on an impedance based medical device using the electromagnetic dynamic registration and/or secondary electromagnetic dynamic registration. The shift and/or drift corrected locations of the electrodes 30 can account for the impedance based shift and/or drift associated with the impedance locations of the electrodes 30 to provide shift and/or drift corrected locations of the electrodes 30 that have any impedance shift and/or drift factored out. As such, the impedance based medical device (which in some embodiments only includes electrodes 30 and does not include magnetic position sensors 28) can be used in an area of interest that has had an electromagnetic dynamic registration computed and/or secondary electromagnetic dynamic registration computed for it.

With further reference to FIG. 1, embodiments of the present disclosure can include a system 10 for generating a registration between impedance and magnetic based coordinate systems. In some embodiments, the system 10 can include a first catheter that includes a first electrode 30 and a magnetic position sensor 28. In some embodiments, the system 10 can include a second catheter that includes a second electrode. In some embodiments, the second catheter can be an impedance only device, as discussed herein, and may not include a magnetic position sensor 28.

In some embodiments, the system 10 can include a main control 12 that includes a processor and memory storing non-transitory computer-readable instructions, as discussed herein. The instructions can be executable to compute a location of a number of fiducial points. The fiducial points can include impedance locations of the first electrode in an impedance based coordinate system and magnetic locations of the magnetic position sensor in a magnetic based coordinate system. The instructions can be executed to compute a global electromagnetic transformation based on the location of the number of fiducial points. The global electromagnetic transformation can be used to transform the impedance location of the first electrode in the impedance based coordinate system into a transformed impedance location of the first electrode in the magnetic based coordinate system. For example, impedance based coordinates of the impedance location of the first electrode in the impedance based coordinate system can be transformed into magnetic based coordinates.

The instructions can be executed to determine a magnetic location of the first electrode in the magnetic based coordinate system, as discussed herein. The instructions can be executed to determine whether an impedance shift and/or drift exists between the transformed impedance location of the first electrode in the magnetic based coordinate system and the magnetic location of the first electrode in the magnetic based coordinate system. In some embodiments, if the coordinates of the transformed impedance location of the first electrode in the magnetic based coordinate system vary from the magnetic location of the first electrode in the magnetic based coordinate system by a defined amount, a shift and/or drift can be declared. In some embodiments, the instructions can be executed to generate an electromagnetic dynamic registration between the impedance based coordinate system and the magnetic based coordinate system based on the impedance shift and/or drift.

In some embodiments, the instructions can be executed to determine a shift and/or drift corrected location of the second electrode based on the electromagnetic dynamic registration. For example, data collected via the first catheter (e.g., registration catheter) can be used to generate the electromagnetic dynamic registration for a volume of interest. When the electromagnetic dynamic registration has been generated, the second catheter that includes the second electrode can be navigated through the volume of interest and shift and/or drift corrected locations for the second electrode can be computed to compensate for any shift and/or drift that is occurring.

Figure 6A:
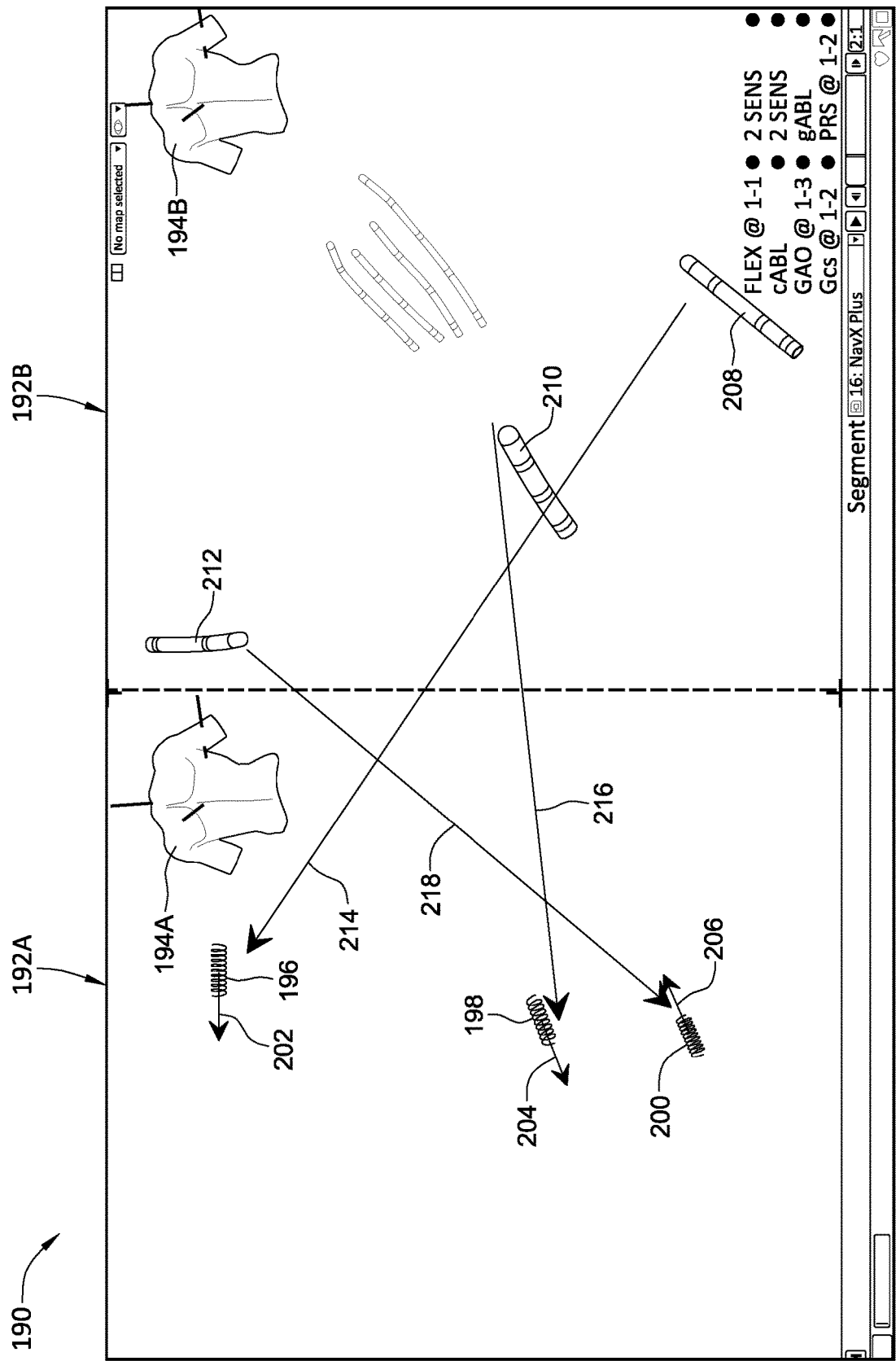
FIG. 6A depicts a graphical user interface displaying a step associated with transformation from an impedance based coordinate system to a magnetic based coordinate system, in accordance with embodiments of the present disclosure.

FIG. 6A depicts a graphical user interface 190 (e.g., display 16) displaying a step associated with transformation from an impedance based coordinate system to a magnetic based coordinate system, in accordance with embodiments of the present disclosure. In some embodiments, FIGS. 6A and 6B illustrate application of Rodrigue's rotation model, as discussed herein. In an example, the graphical user interface 190 displays a magnetic space in a first view 192A and an impedance space in a second view 192B. A perspective that is included in the first view 192A and second view 192B can be indicated by perspective indicator 194A and perspective indicator 194B, respectively. For example, as depicted by the perspective indicators 194A, 194B first view 192A and second view 192B are from a frontal perspective of a patient's body.

The first view 192A displays three magnetic position sensors 28 in the magnetic space. For example, the first view 142A displays a first magnetic coil 196, second magnetic coil 198, and a third magnetic coil 200 in the magnetic space. An orientation of the coils are represented by a first vector 202 passing through the first coil 196, a second vector 204 passing through the second coil 198, and a third vector 206 passing through the third coil 200. A position of the coils and the orientation of the coils can be determined, as discussed herein.

The second view 192B displays a first catheter 208, a second catheter 210, and a third catheter 212. In some embodiments, the catheters 208, 210, 212 can be impedance based devices and may only include impedance based position sensors (e.g., electrodes 30) and may not include magnetic position sensors 28. Embodiments of the present disclosure can transform the locations of each of the catheters 208, 210, 212 from the impedance coordinate system to the magnetic coordinate system, as discussed herein.

FIG. 6B depicts a graphical user interface displaying a second step associated with transformation from an impedance based coordinate system to a magnetic based coordinate system, in accordance with embodiments of the present disclosure. In an example, with reference to FIG. 6B, the locations of the electrodes 30 on the first catheter 208 have been transformed into the magnetic space (e.g., from the impedance based coordinate system to the magnetic based coordinate system).

Figure 7:
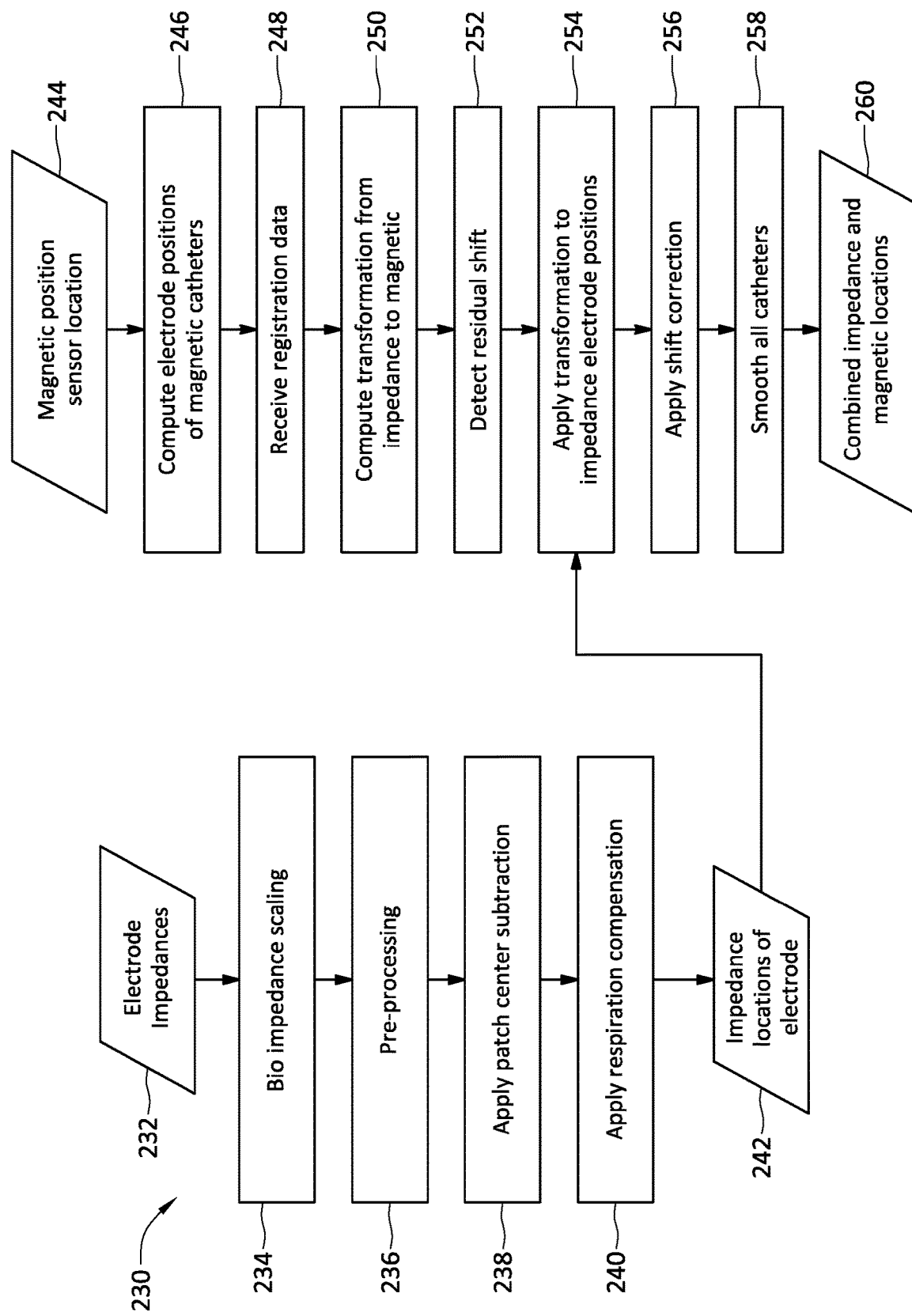
FIG. 7 depicts a flow diagram associated with registering an impedance based coordinate system and a magnetic based coordinate system, in accordance with embodiments of the present disclosure.

FIG. 7 depicts a flow diagram 230 associated with registering an impedance based coordinate system and a magnetic based coordinate system, in accordance with embodiments of the present disclosure. The flow diagram 230 can include similar steps to the flow diagram 38 discussed in relation to FIG. 2. In some embodiments, the flow diagram 230 can include computing a number of fiducial points. The fiducial points can include impedance locations of an electrode 30 and magnetic locations of magnetic position sensor 28. The fiducial points can be collected with a registration catheter, in some embodiments, that includes one or more electrodes 30 and one or more magnetic position sensors 28. At box 232, an impedance signal can be received from electrode 30, which can include data that is representative of a position and/or orientation of the electrode 30. In some embodiments, the impedance signal can be filtered or unfiltered. Bio impedance scaling can be performed at box 234, as discussed in relation to FIG. 2.

At box 236, in some embodiments, pre-processing steps can be performed on the impedance signal. In some embodiments, the steps associated with box 42 depicted in FIG. 2 can be performed to convert the impedance to a location of the electrode in the impedance based coordinate system. However, this step can be optional and further processing of the impedance signal can be performed without converting the impedance signal to a location of the electrode in the impedance based coordinate system. In some embodiments, a model can optionally be applied to the catheter (e.g., distal stabilize) in a pre-processing step, as discussed herein. In some embodiments, a smoothing function can optionally be applied to the impedance signal received from the one or more electrodes 30 disposed on the catheter, as discussed herein. Patch center subtraction can be applied, at box 238, to help reduce shift and/or drift associated with the impedance locations of the electrodes 30. Respiration compensation can be applied at box 240 via data obtained from patient reference sensor 26, as discussed herein, to obtain the impedance locations of the electrodes 30, at box 242.

As discussed, the fiducial points can also include magnetic locations of magnetic position sensor 28. The magnetic locations of the magnetic position sensor 28 can be computed at box 244, based on signals received from the magnetic position sensor 28. A signal can be generated by the magnetic position sensor 28 based on the strength of the magnetic field and the position of the magnetic position sensor 28 in the magnetic field. In some embodiments, a magnetic location of the electrode 30 in the magnetic based coordinate system can be computed at box 246. In an example, the magnetic location of the electrode 30 in the magnetic based coordinate system can be different than the impedance location of the electrode 30 if shift and/or drift is present. The magnetic location of the electrode 30 can be a determined location of the electrode that is based off of a known position and orientation of the one or more magnetic position sensors 28 in the magnetic based coordinate system, in some embodiments. Because the magnetic based coordinate system and the magnetic position sensor 28 are not susceptible to shift and/or drift, the magnetic location of the electrode 30 can reflect a more precise, if not an actual physical location of the electrode 30.

In some embodiments, the flow diagram can include receiving registration data at box 248. In an example, receiving the registration data can include receiving the impedance locations of the electrodes 30 and/or the impedance signal from the electrodes 30 after the patch center subtraction has been applied to the impedance locations of the electrodes 30, but prior to the respiration compensation being applied to the impedance locations of the electrodes 30. In addition, receiving the registration data can include receiving the magnetic locations of the electrodes 30. For example, as discussed herein, the magnetic locations of the electrodes 30 can be determined in the magnetic based coordinate system. The registration data can be collected so the magnetic locations of the electrodes 30 can be registered with the impedance locations of the electrodes 30 (e.g., displayed in one coordinate system). In some embodiments, the impedance locations of the electrodes 30 can optionally be gated to a specific interval of a ventilatory phase, as discussed in relation to FIG. 2.

In some embodiments, the flow diagram 230 can include computing a transformation of the registration data from the impedance based coordinate system to the magnetic based coordinate system at box 250. In some embodiments, the received impedance locations of the electrodes 30 (e.g., that have had patch center subtraction applied) can be compared to the magnetic positions of the electrodes 30 and the impedance based coordinate system and the magnetic based coordinate system can be aligned. A magnetic location that corresponds to the impedance location of the electrodes 30 in the magnetic coordinate system can then be determined. For example, the impedance based coordinates of the impedance location of the electrodes 30 can be transformed into magnetic based coordinates. In an example, the registration data can include both impedance locations of the electrodes 30 in the impedance based coordinate system and magnetic locations of the electrodes 30 in the magnetic based coordinate system. Based on the transformation, the locations of the electrodes 30 can be registered (e.g., combined) in one coordinate system (e.g., magnetic based coordinate system). In an example, Rodrigues' transformation model, an Extended Kalman filter, and/or other methodology discussed herein can provide an instantaneous registration between the impedance based coordinate system and the magnetic based coordinate system. In some embodiments, the flow diagram can include detecting a residual shift and/or drift associated with the impedance location of the electrodes 30, at box 252. For example, a determination can be made of whether any additional shift and/or drift has occurred and/or whether any shift and/or drift still exists, which is unaccounted for.

In some embodiments, the flow diagram 38 can include applying the transformation to the impedance locations of the electrodes 30, at box 254. In an example, applying the transformation can include transforming the impedance locations of the electrodes 30 in the impedance based coordinate system into transformed impedance locations of the electrodes 30 in the magnetic based coordinate system. In some embodiments, the transformation can be computed using the received impedance locations of the electrodes 30 that have had patch center subtraction applied, while the transformation is applied to the impedance locations of the electrodes 30 that have had respiration compensation applied.

In some embodiments, the electromagnetic dynamic registration can be sensitive to location artifacts. While respiration compensation is meant to reduce location artifacts introduced by breathing, it may not do so perfectly. In some systems, magnetic field scaling can include a non-rigid registration of impedance and magnetic coordinate systems using a set of fiducials. The ventilatory cycle causes intra-cardiac catheters to experience motion, resulting in correlated changes in the reported positions in both impedance and magnetic coordinate systems. Simultaneously, the ventilatory cycle introduces artifacts into both magnetic and impedance coordinate systems that are uncorrelated with each other. For example, an anterior PRS rises, falls and tips as the patient breathes, resulting in artifacts in a PRS-referenced coordinate system. The navigational currents of the impedance coordinate system are changed as the lungs empty and fill, resulting in artifacts in the impedance coordinate system. To compute a registration that is not corrupted by ventilatory artifact, fiducial collection can be gated to a signal responsive to the ventilatory phase. If gating operates without error, fiducials can be collected in a standard ventilatory phase.

However, the gating of fiducial collection can slow fiducial data collection. Further, some portions of the navigational volume may only be reached in a particular phase of the ventilatory cycle. Further, there can be a number of issues associated with correctly determining the ventilatory phase and gating. For example, the signal used for gating often experiences level-set changes that are not easily separated from physiologic changes in the frequency domain, which can result in an incorrect gating between the fiducial data collection and the ventilatory phase. There can also be a potential for the phase of artifacts associated with intracardiac catheter positions to indeterminately lead and/or lag that of the signal used for gating. Finally, the signal used for gating can typically be determined in a causal fashion, and is not always predictive of the artifacts on intracardiac catheter positions. Therefore, it can be desirable to compute a registration that is not gated and retrospectively compensates for temporal artifacts, which can be accomplished, as discussed below. Accordingly, embodiments of the present disclosure can employ temporal basis functions to compensate for temporal artifacts.

Generally, a linear regression can be represented as a set of basis functions multiplied by a set of linear weights via the following:

$$Y=B(X)W+\varepsilon$$

In some embodiments, Y represents the dependent variable and is dimensioned $N \times M_Y$, for N samples in $M_Y$ dimensions; X represents the independent variable and is dimensioned $N \times M_X$ for N samples in $M_X$ dimensions; B(X) expresses the basis functions on X, returning a matrix dimensioned $N \times M_B$ for N samples and $M_B$ basis functions; W represents the linear weights on the basis functions and is dimensioned $M_B \times M_Y$; $\varepsilon$ represents the error in dependent samples and has the same dimensions as Y.

For non-rigid registrations, the basis functions can include non-linear functions of X. For example, in thin-plate splines (TPS), the basis functions can be a concatenation of linear and radial basis functions, $$B(X)=[1^N \; X \; \Psi(X)]$$

$$\Psi_{ij}(X)=\varphi(|X_i-C_j|)$$

In some embodiments, C represents a set of control points and is dimensioned $N \times M_X$ and $\varphi(r)$ represents a radial basis function with scalar input and output. The equation of the radial basis function can be determined by $M_X$.

As stated in the above three equations, the independent variable is independent of time. In practice, this is typically not the case. Rather, X is typically a function of time, X(t) and B(X(t),t) are functions of both space and time. Accordingly, some embodiments of the present disclosure can employ a temporal basis function. For example, a temporally periodic offset to a linear set of spatial functions can be expressed via the following equation:

$$B(X(t),t)=[1^N X(t) \cos(\omega t) \sin(\omega t)]$$

In some embodiments, t represents the time associated with the independent variables and is dimensioned N×1. If the basis functions in B(X(t),t) can be separated into independent spatial and temporal functions, then B may be expressed via the following:

$$B(X(t),t)=[F(X(t))G(t)]$$

Examples of spatial basis functions have been given above. In addition to linear basis functions and TPS, other spatial basis function of interest can be those which are harmonic, for example, $\nabla^2(f(x))=0$, as these represent many relevant physics.

Semi-periodic artifacts associated with measurements can be observed as variations about a mean value. To separate variations due to ventilation from that due to cardiac motion or common-mode noise, low-pass filtering can be used to attenuate variation on shorter timescales. For devices which are manipulated by a user, this variation may be obscured by the manipulation, which can occur on timescales similar to ventilation. The impedances observed on cutaneous patches and stable reference catheters are unaffected by user manipulation over suitably long periods of time, as are the positions and orientations of magnetic reference sensors. For these reasons, a multivariate signal responsive to ventilatory artifacts from low-passed cutaneous patch impedances, reference catheter impedances and magnetic reference sensor positions and orientations can be expressed as:

$$S=LP([PR])$$

In some embodiments, LP represents a low-pass filter function; P represents impedance measurements from cutaneous patches and is dimensioned $N_V \times M_P$ for $N_V$ time points and $M_P$ patch measurements per time point. R can represent reference measurements from stable intracardiac catheters and magnetic reference sensors and is dimensioned $N_V \times M_R$ for $M_R$ reference measurements and S represents a signal responsive to ventilatory artifact and is dimensioned $N_V \times (M_P+M_R)$.

In some embodiments, principal component analysis (PCA) can be used to determine a projection of the signal responsive to ventilatory artifact to a low dimensional set of components representing the majority of the variation via the following equation:

$$S-1^{N_V}\overline{S}=U\Sigma V^T$$

In some embodiments, $\overline{S}$ represents the mean of the signal over time and is dimensioned $1 \times (M_P+M_R)$; $1^{N_V}$ represents a column vector of ones dimensioned $N_V \times 1$; $U\Sigma V^T$ represents the singular value decomposition (SVD) such that: $U^T U=I$, $V^T V=I$ and $\Sigma$ is diagonal, with the elements ordered from largest to smallest absolute value, from top-left to bottom-right.

The matrices composing the SVD organize the principal components along their columns such that the principal components decrease in significance from left to right. Thus, the first r principal components are the left-most r columns of U, $\Sigma$ and V, as follow:

$$U = [\; U_r \;\; U_\varepsilon \;]$$

$$\Sigma = \begin{bmatrix} \Sigma_r & 0 \\ 0 & \Sigma_\varepsilon \end{bmatrix}$$

$$V = [\; V_r \;\; V_\varepsilon \;]$$

$$U\Sigma V^T = U_r \Sigma_r V_r^T + U_\varepsilon \Sigma_\varepsilon V_\varepsilon^T$$

By virtue of orthogonality, $V^T V_\varepsilon=0$, thus we may compute the first r principal components of the ventilatory signal as the following equation.

$$(S-1^{N_V}\overline{S})V_r\Sigma_r^{-1}=U_r$$

In some embodiments, basis functions can be created, which do not require filtering to use in conjunction with unfiltered spatial basis functions. The same projection by $V_r\Sigma_r^{-1}$ can be used because the high-frequency components of S are in the null-space of $V_r$. For an arbitrary time point, then, the unfiltered temporal basis function is determined, and represented as follows.

$$([[P(t)R(t)]]-\overline{S})V_r\Sigma_r^{-1}=G(t)$$

While the PCA of reference signals is one example of a set of temporal basis functions. Other temporal basis functions may be used in accord with embodiments disclosed herein.

Once the basis functions are specified, weights on the basis functions can be solved using a least-squares solution to an overdetermined problem. To compute a non-rigid registration that compensates for temporal artifacts, one or more of the following steps can be used. In some embodiments, a set of fiducials points can be collected for each of a plurality of different times. At a single time-point, one or more fiducial points and a set of signals responsive to one or more temporal artifacts can be collected. For each fiducial point, a set of independent variables (e.g., coordinates) can be collected, a set of dependent variables (e.g., coordinates, though impedance values are also relevant) can be collected, and a reference to the signals responsive to temporal artifact can be collected.

In some embodiments, the collected signals responsive to the temporal artifact can be filtered to separate artifacts of interest. For each fiducial point, i, the independent set of variables and signals responsive to temporal artifact at that time point can be substituted into $B(X(t),t)$ to compute $B_i$. Using the dependent set of variables for each fiducial as Y, W can be computed as the solution of $Y=BW+\varepsilon$, which minimizes the sum of squared error, $\|\varepsilon\|$.

As an example where the spatial and temporal basis functions are separable, TPS may be used as the spatial basis functions and the temporal functions may be described by a PCA of low-pass filtered patch and reference catheter measurements as in the unfiltered temporal basis function, as represented above.

In some embodiments, the flow diagram can include determining whether an impedance shift and/or drift exists between the transformed impedance location of the electrode 30 in the magnetic based system and the magnetic location of the electrode in the magnetic based system. As discussed herein, nonlinear shift and/or drift of the impedance location of the electrodes can be due to numerous physiologic phenomena (e.g., local conductivity changes due to saline or lesions, sweat/patch interactions, changes in lung filling, etc.). Because the magnetic position sensors 28 are not subject to shift and/or drift, the computed magnetic locations of the electrodes 30 may not be subject to shift and/or drift. As such, the difference between the location of the transformed impedance location of the electrode 30 in the magnetic based coordinate system and the magnetic location of the electrode can be equivalent to a shift and/or drift of the impedance location of the electrode 30.

In some embodiments, the flow chart can include generating an electromagnetic dynamic registration between the impedance based coordinate system and the magnetic based coordinate system based on the impedance shift and/or drift. The electromagnetic dynamic registration between the impedance based coordinate system and the magnetic based coordinate system can account for the transformation of the impedance locations of the electrodes 30 in the impedance based coordinate system into the transformed impedance locations of the electrodes 30 in the magnetic based coordinate system and can also account for the impedance shift and/or drift associated with the impedance locations of the electrodes 30. Accordingly, impedance locations of the electrodes 30 can be received and the electromagnetic dynamic registration can be used to transform the impedance locations of the electrodes 30 into the magnetic based coordinate system and correct for the shift and/or drift, which can be associated with the impedance locations of the electrodes 30. In an example, impedance shift and drift detection and correction can be performed via the electromagnetic dynamic registration, as detailed in U.S. application No. 62/182,208, titled "Impedance Shift and Drift Detection and Correction", filed 19 Jun. 2015, filed 19 Jun. 2015, which is hereby incorporate by reference in its entirety.

In some embodiments, the electromagnetic dynamic registration can be generated for a volume of interest (e.g., chamber of the heart). In an example, as discussed herein, the registration catheter with the magnetic position sensors 28 and the electrodes 30 disposed thereon can be used to gather data for the generation of the electromagnetic dynamic registration. In some embodiments, once the electromagnetic dynamic registration has been generated for the volume of interest, the registration catheter with the magnetic position sensors 28 and the electrodes 30 can be removed from the volume of interest. In some embodiments, an impedance based medical device, which can be a catheter that includes electrodes 30 and no magnetic position sensors 28, can be inserted in the volume of interest. The electromagnetic dynamic registration can then be used to register an impedance location of an electrode 30 on the impedance based medical device with the magnetic based coordinate system using the electromagnetic dynamic registration and a shift and/or drift associated with the impedance location of the electrodes 30 can be accounted for via the electromagnetic dynamic registration.

In some embodiments, the flow chart can include applying the shift and/or drift correction, at box 256, to determine a shift and/or drift corrected location of the electrodes 30 on the impedance based medical device. As discussed herein, in some embodiments, the impedance location of the electrodes 30 can be shifted via the electromagnetic dynamic registration to provide shift and/or drift corrected locations of the electrodes 30 on the impedance based medical device. In some embodiments, a smoothing function can be applied to the shift and/or drift corrected locations of the electrodes 30 on the impedance based medical device, at box 258. The thin plate spline transformation, as discussed herein, may not provide locations of the electrodes 30 that are associated with a representation of a smooth catheter. As such, a smoothing function can be applied to the shift and/or drift corrected locations of the electrodes 30 to provide an improved representation of the catheter. In some embodiments, the shift and/or drift corrected locations of the electrodes 30, the magnetic locations of the electrodes 30, and/or the magnetic locations of the magnetic position sensors 28 can be combined, at box 260. In an example, the flow diagram can include displaying the shift and/or drift corrected locations of the electrodes 30, the magnetic locations of the electrodes 30, and/or the magnetic locations of the magnetic position sensors 28, as discussed herein.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for electromagnetic dynamic registration for device navigation has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed:

1. A non-transitory computer-readable medium storing instructions to generate a registration between impedance and magnetic based coordinate systems, executable by a processing resource to:
   compute a location of a number of first fiducial points for a volume of interest, wherein the number of first fiducial points include impedance locations of an electrode disposed on a catheter in an impedance based coordinate system and magnetic locations of a magnetic position sensor disposed on the catheter in a magnetic based coordinate system;
   transform the impedance location of the electrode in the impedance based coordinate system into a transformed impedance location of the electrode in the magnetic based coordinate system;
   determine a magnetic location of the electrode in the magnetic based coordinate system;
   determine whether an impedance shift exists between the transformed impedance location of the electrode in the magnetic based system and the magnetic location of the electrode in the magnetic based system;
   generate an electromagnetic dynamic registration between the impedance based coordinate system and the magnetic based coordinate system based on the impedance shift;
   compute a location of a number of second fiducial points outside the volume of interest, wherein the number of second fiducial points include impedance locations of the electrode in the impedance based coordinate system and magnetic locations of the magnetic position sensor in the magnetic based coordinate system; and
   update the electromagnetic dynamic registration based on the second fiducial points via a smoothing function that utilizes affine regularization.

2. The non-transitory computer-readable medium of claim 1, further comprising instructions to determine a secondary electromagnetic dynamic registration in response to a determination that impedance shift exists.

3. The non-transitory computer-readable medium of claim 2, further comprising instructions to register an impedance location of the electrode on the impedance based medical device with the magnetic based coordinate system based on the secondary electromagnetic dynamic registration.

4. The non-transitory computer-readable medium of claim 3, further comprising instructions to correct the impedance shift based on the secondary electromagnetic dynamic registration.

5. The non-transitory computer-readable medium of claim 1, wherein determining a magnetic location of the electrode in the magnetic based coordinate system comprises uses a known physical distance between the electrode and a second electrode disposed on the catheter.

6. A system for generating a registration between impedance and magnetic based coordinate systems in a chamber of a heart, comprising:
   a first catheter that includes an electrode and a first and second magnetic position sensor;
   a processor and memory storing non-transitory computer-readable instructions, executable by the processor to:
      compute a location of a number of first fiducial points for a volume of interest in the chamber, wherein the first fiducial points include impedance locations of the electrode in an impedance based coordinate system and magnetic locations of the first and second magnetic position sensors in a magnetic based coordinate system;

transform the impedance location of the electrode in the impedance based coordinate system into a transformed impedance location of the electrode in the magnetic based coordinate system;

determine a magnetic location of the electrode in the magnetic based coordinate system;

determine whether an impedance shift exists between the transformed impedance location of the electrode in the magnetic based system and the magnetic location of the electrode in the magnetic based system;

generate an electromagnetic dynamic registration between the impedance based coordinate system and the magnetic based coordinate system based on the impedance shift;

compute a location of a number of second fiducial points outside the volume of interest, wherein the number of second fiducial points include impedance locations of the electrode in the impedance based coordinate system and magnetic locations of the first and second magnetic position sensors in the magnetic based coordinate system; and update the electromagnetic dynamic registration based on the second fiducial points via a smoothing function that utilizes an affine regularization.

7. The system of claim 6, further comprising instructions to transform the impedance based coordinates of the impedance location of the electrode in the impedance based coordinate system into magnetic based coordinates.

8. The system of claim 6, wherein the magnetic location of the electrode in the magnetic based coordinate system is determined based on a linear length between the first and second magnetic position sensor.

9. The system of claim 6, wherein the magnetic location of the electrode in the magnetic based coordinate system is determined based on an arc length between the first and second magnetic position sensor.

10. The system of claim 6, further comprising:
a second catheter that includes a second electrode, wherein the second catheter is an ablation therapy device and is a different device than the first catheter.

11. The system of claim 10, wherein the second catheter is an impedance only device.

12. The system of claim 10, wherein the second catheter includes an ablation electrode.

13. The system of claim 10, further comprising instructions to:
determine a shift corrected location of the second electrode by applying the electromagnetic dynamic registration to impedance locations of the second electrode, wherein the electromagnetic dynamic registration is determined with the first catheter; and navigate the second catheter through the chamber of the heart using the shift corrected location of the second electrode.

14. The system of claim 13, further comprising instructions to display the shift corrected location of the second electrode based on the electromagnetic dynamic registration.

* * * * *